(12) United States Patent
Green et al.

(10) Patent No.: US 9,020,587 B2
(45) Date of Patent: Apr. 28, 2015

(54) METHOD AND APPARATUS OF NEUROLOGICAL FEEDBACK SYSTEMS TO CONTROL PHYSICAL OBJECTS FOR THERAPEUTIC AND OTHER REASONS

(71) Applicant: Cerebotix, Inc., Reno, NV (US)

(72) Inventors: George H. Green, Reno, NV (US); John LeMay, Reno, NV (US)

( * ) Notice: Subject to any disclaimer, the term of this patent is extended or adjusted under 35 U.S.C. 154(b) by 0 days.

(21) Appl. No.: 13/676,519

(22) Filed: Nov. 14, 2012

(65) Prior Publication Data

US 2013/0218044 A1    Aug. 22, 2013

Related U.S. Application Data

(63) Continuation of application No. 12/141,275, filed on Jun. 18, 2008, now Pat. No. 8,326,408.

(51) Int. Cl.
*A61B 5/0482* (2006.01)
*A61B 5/048* (2006.01)

(52) U.S. Cl.
CPC ............... *A61B 5/0482* (2013.01); *A61B 5/048* (2013.01)

(58) Field of Classification Search
None
See application file for complete search history.

(56) References Cited

PUBLICATIONS

Schalk et al (IEEE Transactions on Biomedical Engineering, 2004, 51:1034-1043).*
Zhang et al (Computational Intelligence and Neuroscience—EEG/MEG Signal Processing, 2007, vol. 2007, 9 pages).*
Thatcher et al (Clinical Neurophysiology, 2005, 116:2129-2141).*

* cited by examiner

*Primary Examiner* — Laura B Goddard
(74) *Attorney, Agent, or Firm* — Holland & Hart LLP

(57) ABSTRACT

A method and apparatus using brainwaves to control real objects is provided. The method and apparatus comprise using sensors to detect the brain's electrical signals and transmit at least two brainwaves to an apparatus that converts the brainwaves into a format usable by a signal processor. The signal processor determines a coherence between portions of the brainwaves, typically in the frequency domain, and compares the coherence values, which change rapidly from moment to moment, to thresholds. Based on the comparison of the coherence value to the thresholds, which are adjusted over time based on feedback relating to success, a control signal is developed that can be sent to a real object to control 3 dimensional motion of the control object.

9 Claims, 6 Drawing Sheets

METHOD AND APPARATUS OF NEUROLOGICAL FEEDBACK SYSTEMS TO CONTROL PHYSICAL OBJECTS FOR THERAPEUTIC AND OTHER REASONS

CROSS-REFERENCE TO RELATED APPLICATION

This application is a continuation of, and claims priority through, applicant's prior U.S. patent application Ser. No. 12/141,275, filed Jun. 18, 2008, entitled "Method And Apparatus Of Neurological Feedback Systems To Control Physical Objects For Therapeutic And Other Reasons," which prior Application is hereby incorporated herein by reference in its entirety.

BACKGROUND

1. Field

The technology of the present application relates generally to neurological feedback systems, and more specifically to using neurological systems to control physical objects for therapeutic and other reasons.

2. Background

Biofeedback has been a known conditioning and therapeutic technique for years. Generally, the treatment and training provides a sensor to identify or monitor a physiological condition, such as electrodermal or galvanic skin response (EDR or GSR), heart rate variability (HRV), or the like, and a display, such as a computer or television screen. A control processor receives the sensor information and, in many simplistic devices, adjusts the displayed response to encourage an appropriate response. For example, a resting HRV may provide a balloon image on a display floating high above a landscape. As the patient's or subject's HRV becomes more indicative of agitation, the balloon may fall closer to the horizon on the display.

Another type of biofeedback relates to the electrical functioning of the brain and is generally referred to as neurofeedback. Brain functions generate electrical signals (brainwaves) that may be sensed by electrodes typically in close proximity to the skull. Controlling the brainwaves or conditioning the brain to produce certain types of brainwaves is believed to facilitate wellness. In this regard, neurofeedback is of particular interest to psychologists and the like as the brain is the central organ that controls emotions, physical actions, thoughts, and behaviors. Thus, it is believed that influencing the brain to produce particular types of brainwaves may facilitate corrective training for various disorders, such as, for example, anxiety, depression, attention deficit and hyperactivity disorder, Asperger's syndrome, obsessive compulsive disorder, and the like.

Using an electroencephalograph (EEG) in conjunction with computer processors allows precise and fast determination of brainwave activity. Generally, brainwaves are classified into five generic categories:

1. Brainwaves having a frequency of 2 to 4 hertz are generally referred to as Delta waves;
2. Brainwaves having a frequency of 4 to 8 hertz are generally referred to as Theta waves;
3. Brainwaves having a frequency of 8 to 12 hertz are generally referred to as Alpha waves; and
4. Brainwaves having a frequency of 12 to 26 hertz are generally referred to as Beta waves; and
5. Brainwaves having a frequency of 26 to 50 hertz are generally referred to as Gamma waves.

These brainwaves are measured by sensing the electrical signals of the brain using electrodes. The electrical signals sensed by the electrodes are passed through band pass filters to isolate brainwaves in particular frequency ranges to establish the Delta, Theta, Alpha, Beta and Gamma wave sets. Typically, Delta waves are associated with deep sleep brain activity. Theta waves are often associated with a transitional phase between sleep and wakefulness. Alpha waves are typically associated with periods relaxation, such as, for example, meditation. Beta waves are associated with concentration and task specific activities.

One popular way to analyze brainwaves is to measure the coherence or discoherence (also referred to as non-coherence and incoherence) between the brainwaves from various portions of the brain in a particular frequency range. For example, a person's Alpha waves from two different regions of the brain can be compared. The degree of similarity between the Alpha waves of the two regions would determine the degree of coherence.

Not uncommon today, a person undergoing neurofeedback treatment uses a video display to provide real-time visual feedback in response to detected brainwave activity. A computer processes the brainwaves and compares the actual brainwave to a normalized or desired pattern. The "closeness" to the normalized or desired pattern provides an input to the processor controlling the video display. Based on the desired activity, the video may behave in a pattern to induce the user to alter the user's brainwave. Thus, the visual feedback can be used to condition the brain to produce a desired brainwave pattern matched to a normalized or desired brainwave pattern. Recently, a trend has existed that uses the information to control video in simulations more akin to game playing than therapeutic exercises. Today's technology regarding using brainwaves in neurofeedback therapeutic devices and/or game playing, however, is relatively unsatisfactory. In particular, due in part to the rapidity that brainwaves change, the brainwave coherence values provide at best an unstable signal to control video. Moreover, the instability of the signal makes it difficult or virtually impossible to control a physical device based on brainwave activity. However, for at least improved therapeutic results, it would be preferable to provide a real vs. virtual visual feedback mechanism. Moreover, for both game playing and therapeutic systems, brainwaves typically change overly rapidly for a fine-tuned control, thus today's systems generally have only sluggish, course controls that are unsatisfactory for either games or therapies.

Thus, against this background, it would be desirous to provide a method and system of using brainwaves to provide improved therapeutic and game-playing controls.

SUMMARY

Aspects of the technology of the present application disclosed herein address the above stated needs by providing a method of training a patient/user to produce desired brainwave patterns. The method of training comprises obtaining two or more brainwave signals from a patient/user. The brainwave signals are separated into corresponding bands and compared to determine a coherence between the brainwave signals. The coherence between the signals is compared to a predetermined threshold to determine whether the brainwave signals are behaving in a desired manner. Based on comparison to the threshold, a control signal output is provided to a control object that moves based on the control signal. Controlling at least one control object using at least one control signal based on the comparison, such that the control object moves and provides visual feedback to the patient tending to cause the user to produce desired brainwave in response to a neurological condition.

Another aspect of the technology provided in the present application includes converting the brainwave signals into the frequency spectrum and filtering the brainwaves into a number of frequency bands for which a coherence determination is desired. Each of the coherence values is used in a comparison to a threshold to develop a plurality of control signals to a control the physical motion of an object.

Another aspect of the technology relates to converting brainwaves into control signals that can be wirelessly transmitted to a remote object. The control signals direct the motion of the remote object.

In one aspect, the technology of the present application may be applied to video simulations, such as, gaming inputs to control virtual objects. The input directs the motion of the virtual object and/or the difficulty of the background associated with the game.

In still another aspect of the technology, the present application provides mechanisms to allow brainwaves to control prosthetics such as, for example, artificial arms and legs. The technology may allow for individual training to produce brainwaves that are converted to electrical control signals to operate the prosthetics. The electrical control signals may be provided wirelessly or wired.

Another aspect of the technology provides cognitive feedback to a person using the device. The cognitive feedback relates to sensory input that may tend to cause the brain to produce the desired brainwave patterns. The sensory input may include visual feedback based on a video monitor and real object motion.

The technology of the present application also provides non-cognitive feedback to a person using the device. The non-cognitive feedback relates to sensory and non-sensory input that may tend to cause the brain to produce the desired brainwave patterns. The non-cognitive feedback may include low frequency sound, rapid visual stimulation, electrical impulse, and feedback altering processing values to more readily allow the user to achieve the desired goals.

Still another aspect of the technology provided in the present application includes an apparatus to provide a binaural beat to induce a patient/user to produce brainwaves in a particular frequency range.

It is to be understood that the scope of the invention is to be determined by the claims as issued and not by whether a given embodiment includes any or all features set forth in this Summary of by whether a given embodiment addresses any or all issues identified in the Background of this Application. There are additional aspects of varying embodiments of the present application. These additional aspects are apparent to one of ordinary skill in the art on reading the disclosure set forth below and as set forth in the claims herein.

DETAILED DESCRIPTION

Figure 1:
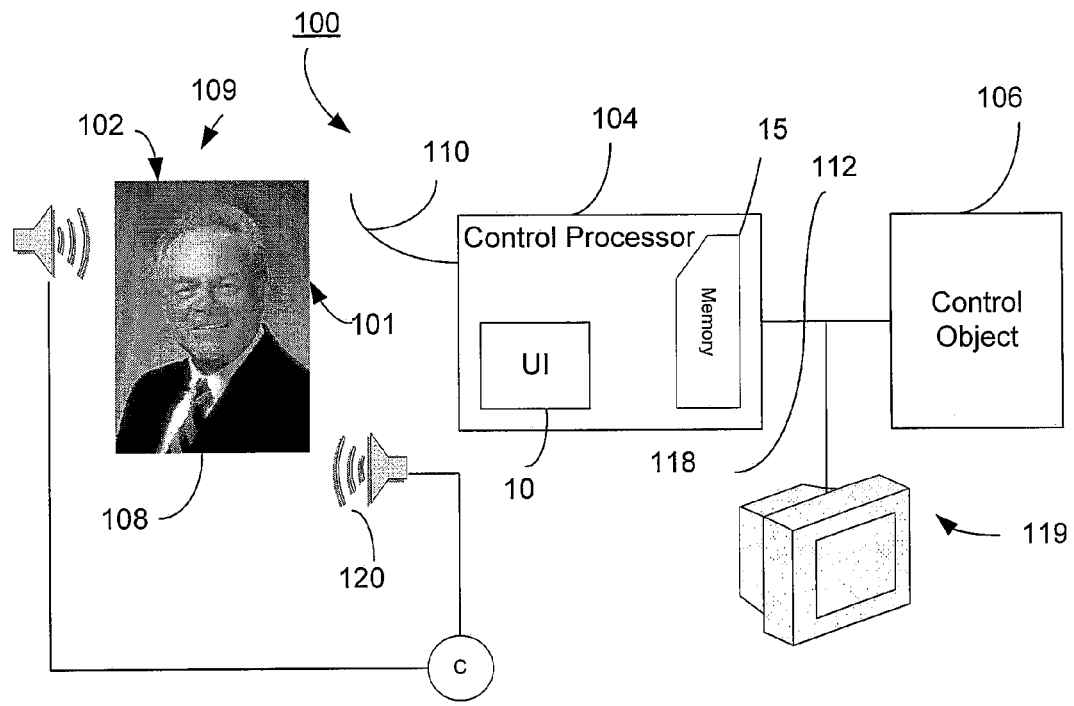
FIG. 1 is a functional block diagram of an exemplary embodiment of the technology of the present application.

The technology of the present application will now be explained with reference to the figures. The figures which disclose various exemplary embodiments of the technology generally relate to a method and apparatus designed to use brainwaves to control objects or inputs to control systems. In one exemplary embodiment, the apparatus and method can be used to control real objects, such as a remotely operated car, vehicle, keyboard, prosthesis, or the like. In other exemplary embodiments, the apparatus and method provide control signals to virtual objects. In still other exemplary embodiments, the apparatus and method provide control signals to both real and virtual objects. In general, the technology of the present application, however, is described in relation to therapeutic uses. One of ordinary skill in the art, however, on reading the disclosure herein would understand the technology of the present application has many non-therapeutic uses, such as, for example, thought-controlled remote exploration, thought-controlled input/output devices for interaction between disabled people, thought-controlled input to electro-mechanical prosthesis devices, and the like. The word "exemplary" is used herein to mean "serving as an example, instance, or illustration." Any embodiment described herein as "exemplary" is not necessarily to be construed as preferred or advantageous over other embodiments. Moreover, all the embodiments described herein should be considered exemplary unless specifically noted otherwise.

Generally, the term telekinesis refers to the ability to influence objects solely through the use of the mind. The technology of the present application is not telekinesis, but rather uses the energy of the cerebrum to provide inputs to a processor. The processor processes the inputs and provides control signals that influence the objects. The process of using brainwaves as inputs to a control processor to control and object may be referred to as cerebral robotics or CEREBOTIC control.

Brainwaves are derived from any animal with brain functionality. While it could be used on numerous animals, the technology of the present application is described with particular reference to a human. For ease of reference, the brainwaves may be obtained from a player, user, subject, patient, or the like, which are generally used interchangeably herein.

As mentioned above, conventionally, brainwave coherence, or incoherence (also referred to as discoherence or non-coherence), is measured by comparing a patient's brainwave coherence values calculated between two regions of the cerebral cortex (or outer brain) against normalized brainwave coherence values. The technology of the present application, however, measures coherence between multiple parts of a single brain and compares them to values associated with improvement. For example, a processor compares the patient's left hemisphere Alpha wave to the patient's right hemisphere Alpha wave to determine coherence between the left and right hemispheres of the brain. Alternatively, coherence may be measured between two areas of the brain that may operate cooperatively for a particular task, the areas may be left/right hemisphere, front-left/back-left portions of the brain or the like. Designations of left, right, front, and back as used herein should not be considered limiting for purposes of the technology of the present application, but rather as a relative location. A left hemisphere brainwave and right hemisphere brainwave, for example, could easily be considered a first brainwave and a second brainwave.

As mentioned above, one aspect of the technology of the present application relates to using the technology to improve therapeutic training of the brain. Thus, the present application is described largely in relation to therapeutic aspects of the technology. However, one of ordinary skill in the art will recognize on reading the present disclosure that the technology of the present application may be used for alternative applications, such as, for example, game input, remote operating equipment, prosthesis control, and the like.

Referring now to FIG. 1, a functional schematic diagram is provided that generally outlines a therapeutic system 100. The therapeutic system 100 includes one or more patient brainwave sensors 102 supported proximate a patient 108, a control processor 104 (which is shown as one component in FIG. 1, but as will be understood from the below may in fact be several distinct processors or a single integrated unit), and a control object 106. Patient 108 would be provided with sensors 102 to detect electrical activity of the patient's brain (not specifically shown). The sensors 102, or electrodes, may be individually adhered to the patient 108 or provided in a support 101, such as for example, a helmet, headband, or other head wear as a matter of design choice. For therapeutic use, it may be beneficial to provide sensors as individual electrodes and not in a pre-developed helmet, for example, to facilitate placement around the skull as desired by the doctor, therapist, or the like.

The actual sensors 102 and placement of the sensors 102 are generally within the ordinary skill in the art and will not be further explained except for completeness relating to the technology of the present application. The sensors 102, which may include a processor 109 to preprocess the sensed electrical signals, transmit the signals to control processor 104 through a communication link 110. Communication link 110 may be a cable, bus, ribbon cable, solder connection, wireless transmission, or the like. If a wireless transmission, sensors 102 would require a RF transmitter, such as, a Bluetooth transmitter, Zigbee transmitter, or the like, and an associated antenna. Control processor 104 would similarly require a corresponding RF receiver and antenna. Control processor 104 and control object 106 are connected by communication link 112. Similar to communication link 110, communication link 112 may be a cable, bus, ribbon cable, solder connection, wireless transmission, or the like. To facilitate control of a real object (vs. a virtual object), communication link 112 as a wireless link may provide greater potential range of motion. If control object is a virtual object, such as a display 119, a cable connection may be sufficient. The communication links 112 and 110 may sometimes be referred to as data links. The communication links 112 may be networked connections such as, for example, through a LAN, WAN, WLAN, WWAN, WiFi, Internet, Ethernet, personal area network or PAN, a private network, or the like.

Figure 3:
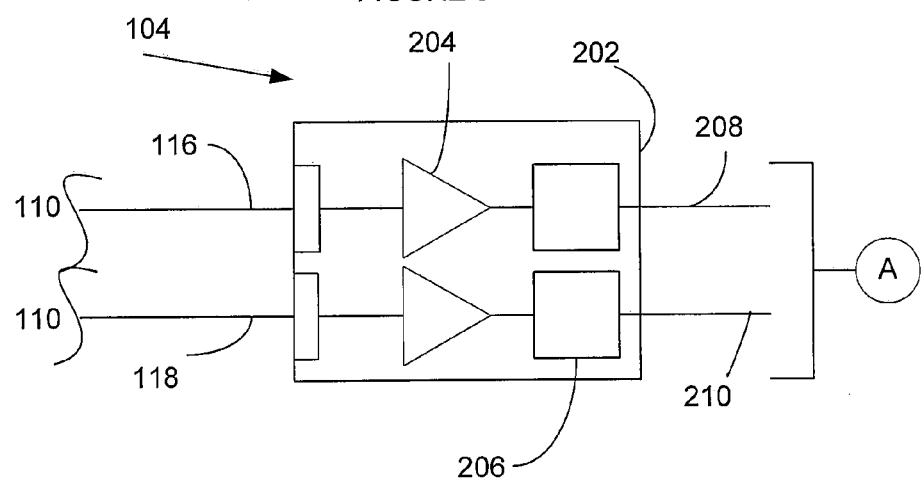
FIG. 3 is a is a functional block diagram of extracting signals from a patient in accordance with the technology of the present application.

As described above, and as shown in FIG. 1, sensors 102 are arranged to pick up a left hemisphere brainwave and generate a corresponding left hemisphere brainwave signal 116 and to pick up a right hemisphere brainwave and generate a corresponding right hemisphere brainwave signal 118 (see FIG. 3 showing signals being transmitted to control processor 104). The left hemisphere brainwave signal 116 and the right hemisphere brainwave signal 118 are sometimes referred to as first or second brainwave signal and collectively as brainwave signals. For example, sensors 102 may be arranged in various combinations, but one exemplary placement of sensors 102 includes three sensors at CT3, Cz, CT4 (which is halfway between International 10-20 sites C3-T3 and C4-T4) and two reference sensors at A1 and A2.

The individual signals are input to control processor 104. Control processor 104, as will be explained in more detail below, processes the signals to develop control output signals 118 transmitted to control object 106. While shown in FIG. 1 as a single control processor 104, control processor 104 may be several independent processors connected via a network, such as, for example, an Ethernet, a LAN, a WAN, a WLAN, WiFi, Internet, or the like. Control processor 104 controls the major functions of the therapeutic system 100 including providing computing functionality to process the inputs (brainwaves signals) and/or data required for operation of the therapeutic system 100. Control processor 104 may include a user interface 10 to allow a therapist or the like to interact with the processes described below to manually adjust various settings, inputs, and the like. User interface may comprise a typical interface for such a device including keyboards, alphanumeric pads, mouse, track balls, light pens, touch screens, voice recognition, microphones, speakers, and the like. Moreover, control processor 104 may include one or more memory banks 15 connected or integrated into control processor 104 or the additional components associated with control processor described below. Memory 15 may be volatile and/or nonvolatile memory on any suitable media. Memory 15 may include code, routines, modules, or the like to allow control processor to perform various operations and functionality as herein described.

Figure 2:
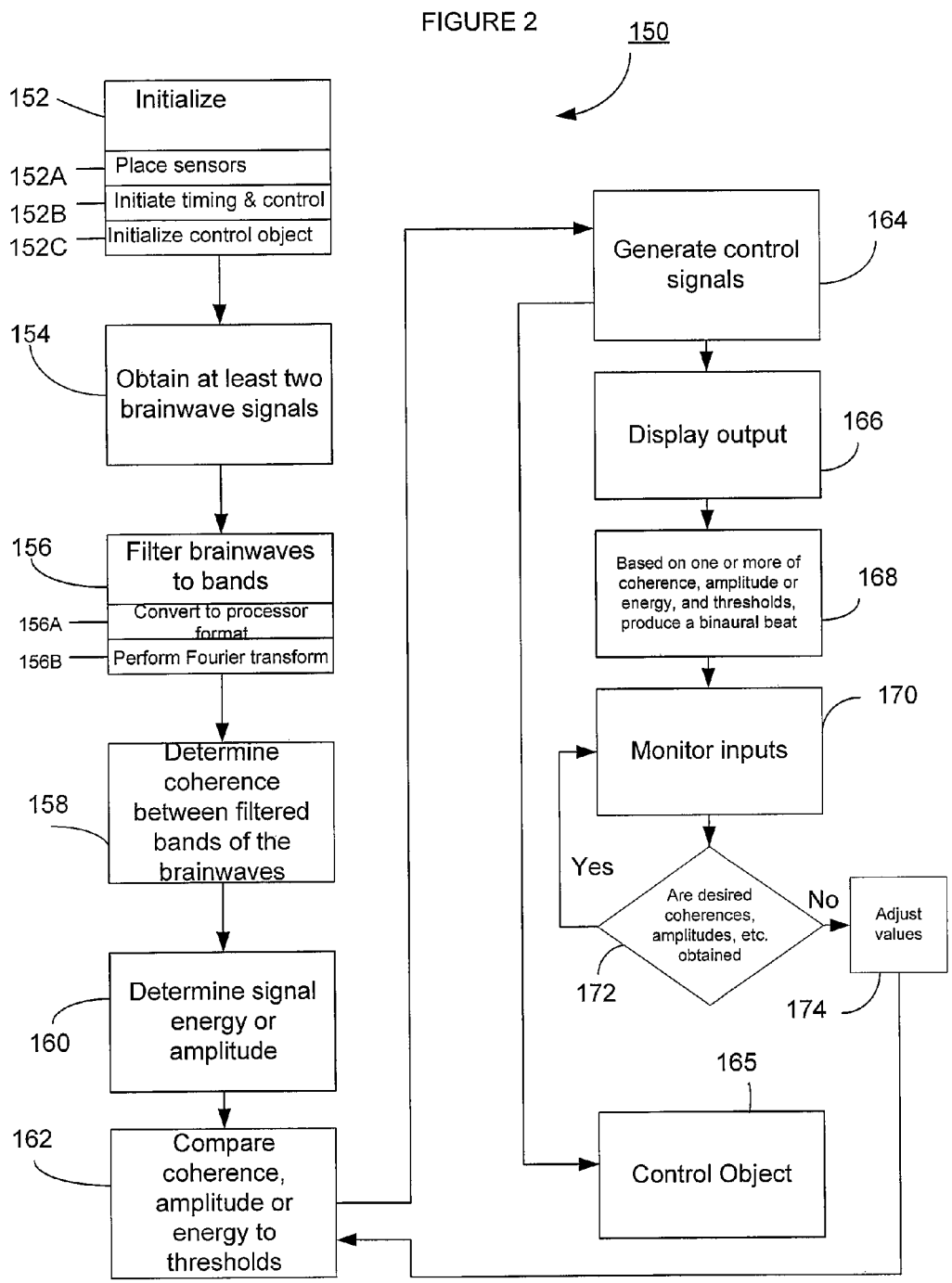
FIG. 2 is an exemplary methodology using the technology of the present application.

Referring now to FIG. 2, an exemplary method 150 of operating therapeutic system 100 will be explained. While method 150 is described as comprising discrete steps or actions in a particular order, the steps outlined below are provided in an exemplary order for ease of understanding. The methodology outlined may be executed in more, less, and different steps arranged in the same or different orders. Additionally, the methodology described herein may be a substantially continuous process where the steps are performed substantially simultaneously, or discretely as described.

Method 150 will be explained in context of providing therapeutic influence to assist an individual (patient 108) to produce brainwave patterns to minimize the effects of a neurological disorder. However, the system could likely be used to train patient 108 to produce brainwaves to augment a particular neurological effect as well. Also, the methodology 150 could be used for other than therapeutic matters, such as, for example, game input, prosthesis control, or the like.

Referring specifically to FIG. 2, the method is initialized at step 152. Initializing the method may include the step of placing sensor 102, step 152A, initiating timing and control of the processors, step 152B, initiating the control object 118, step 152C, and the like. Once initiated, therapeutic system 100 begins obtaining at least two brainwave signals from at least two sections of the brain, step 154. The methodology and system 100 described herein generally refers to a left hemisphere brainwave signal and a right hemisphere brainwave signal as an example, but the two brainwave signals may be generated from any two portions of the brain as desired. The raw brainwave signals are provided to a filtering system to filter the brainwaves into frequency bands, step 156. Filtering the brainwaves into frequency bands may include converting the brainwave signal into a format usable by a signal processor, step 156A, performing a Fourier transform on the brainwave signal, step 156B, and the like. The filtering may be accomplished by any number of conventional devices, such as, for example, low pass, band pass, and high pass filters as are commonly understood in the art.

The technology of the present application is described with relation to therapeutic uses. Thus, in accordance with conventional therapeutic methodologies, the brainwaves are described as being filtered into an Alpha Theta range, a sensory motor rhythm range, a Beta range, and a Gamma range. Once filtered into frequency bands, a coherence between the two brainwave signals in each band is determined, step 158. Notice, distinctly unlike conventional therapeutic methodologies that compare coherence of a patient's brainwave to a normative database, the present application compares two brainwave signals of the patient for a trend in the coherence towards or away from a "therapeutic" value. Such a therapeutic value may include, for example, that once Alpha wave coherences is above 75% it does not fall below 70% coherence. For example, the left hemisphere brainwave produces, after filtering, an Alpha Theta range signal and the right hemisphere brainwave produces, after filtering, an Alpha Theta range signal. The left and right hemisphere Alpha Theta range signals would be compared to determine a coherence between the signals. The coherence would be used to determine whether coherence is moving towards the therapeutic goal. Conventional methodologies would typically compare the left, right, or a combination of the Alpha Theta range to a normative signal in a database. The technology of the present application, however, in the first instance does not compare any brainwave coherences to a normative database of brainwave coherence.

In addition to coherence, another therapeutic value that may be measured is the amplitude or energy of a particular wave form. Thus, at step 160, the amplitude or energy of a signal is determined. The signal may be total energy of the left hemisphere signal, total energy of the right hemisphere signal, total energy of the left and right hemisphere signal, energy of the Alpha Theta brainwaves, or any possible combination thereof.

Using the coherence values, amplitude or energy values, or a combination thereof, method 150 compares the values against one or more threshold values, step 162. As can be appreciated, brainwave signal changes are generally rapid. Thus, the coherence value is often changing rapidly and is difficult to monitor, making it especially difficult to provide stable control signals to control the motion of real objects. However, by comparing coherence, amplitude or energy, to a threshold value, an output signal based on the comparison may remain constant over an extended period. For example, Alpha Theta coherence may be trending in an upwards direction, but frequently dips into a downwards direction (i.e., incoherence or discoherence) on its trend toward more coherence. Thus, although the actual coherence value may be in flux, the coherence above a threshold or the coherence trending up, is typically not changing as rapidly as the actual value. The output of the comparisons of coherence, amplitude or energy, or a combination thereof to thresholds including, for example, whether coherence is above a particular minimum value or below a particular maximum value, whether coherence values are increasing or decreasing, whether energy of the signal is above a minimum signal or below a maximum signal, or the like, or some combination thereof, is used to generate control output signal, step 164. The control output signal may provide 2 or 3 dimensional control signals, such as, for example, a thrust, rotation, and lift signal, multiple thrust signals, a movement vector in the X,Y,Z plane, a movement vector in the X,Y plane, any other type of movement vector, or the like to control an object, step 165. Some exemplary operational and functional steps associated with developing the various control signals of a present prototype are provided below. Throughout the process of methodology 150, a display screen or monitor 119 may provide various display various signals, step 166. An exemplary display output will be explained further below in connection with FIG. 7. The display output may be used as visual feedback to the patient 108. The display may include, for example, raw brainwave EEG signals, coherence signals, control signals, threshold displays, and the like as will be explained in connection with FIG. 7. During the operation of methodology 150, and generally in relation to coherence values and threshold values, a binaural beat may be generated, step 168. The binaural beat generated non-cognitively provides feedback tending to influence the patient's brain to produce desired brainwaves or brainwave patterns. A neural network (sometimes referred to conventionally as auto-logic cascade or fuzzy logic) monitors the system, for example, the coherence, amplitude or energy, or thresholds or a combination thereof, step 170. Based on the monitoring, it is determined whether the desired brainwave functions are being obtained, step 172, i.e., or the desired thresholds are being met or the like. If it is determined that the thresholds are not being met or being met too readily, the threshold is adjusted based on a predetermined adjustment algorithm, step 174. For example, one possible threshold consideration is a determination regarding whether Alpha Theta brainwave coherence is increasing. The threshold for this value may be adjusted depending on whether the patient is successful in causing the increase in coherence to exceed the required threshold. If, for example, it is determined the patient cannot successfully obtain the Alpha Theta coherence at the initial threshold, the threshold is lowered (or raised) until the patient can in fact meet the threshold.

The feedback loop described above as an auto logic cascade includes components of fuzzy logic that combines a simple logic feedback systems with a linear feedback system to adjust the threshold values associated with the coherence and energy levels. These controls are used to adjust both the input threshold controls and the output threshold control assist. For example, one therapeutic goal is to increase Alpha Theta coherence. If Alpha Theta coherence is low such that the initial threshold is not exceeded within a predetermined timeframe or not exceeded and maintained for a predetermined timeframe, the fuzzy logic feedback loop may in the first instance allow the threshold variation and in the second instance reduce the required coherence threshold to an achievable level. The amount the threshold is lowered may be, for example, based on an iterative process until the threshold is achieved, for example, or on other control algorithms. Similarly, the feedback loop may increase the threshold if the coherence value exceeds the threshold by a certain amount, consistently for a predetermined timeframe, or overly rapidly, some combination thereof or the like.

Another exemplary feedback may be related to another therapeutic goal of increasing Alpha Theta coherence while decreasing Beta coherence (frequency separation). In the first instance, the feedback loop would determine whether Alpha Theta coherence is satisfactorily exceeding its threshold. Next, the feedback loop would determine whether the separation between the coherences is above a desired separation. Depending on the adjustment algorithm, the separation threshold may be increased or decreased. Changing the threshold of frequency separation may influence whether the initial thresholds are still being satisfactorily achieved.

Thus, as can be seen, the feedback loop in one exemplary embodiment reacts to a series of inputs to adjust threshold values. The first input should be performed satisfactorily before evaluating and adjusting the second input, etc. Moreover, each adjustment causes a reevaluation of the preceding thresholds to compensate for any influence that adjusting later thresholds may have on previous thresholds. While identified as sequential in nature, the feedback loop may operate sequentially, in parallel, or a combination. Moreover, multiple feedback loops may be established to control for various desired results. For example, in the method 150 described, separate feedback loops or cascades may be established for each of the coherence, amplitude, etc. measurements.

One of ordinary skill in the art will recognize on reviewing the above that display output (step 166) and control object (step 165) provide visual feedback to the patient. For example, if increased Alpha Theta coherence causes lift of an object, the object's movement up or down would provide visual, cognitive feedback to the patient. Similarly, display output would function in a similar way. As will be explained in connection with FIG. 7 below, certain features of the display output may increase the ability of the patient to control the real object although the therapeutic effect and training of the brain is generally enhanced by control of the real object. Steps 168 to 174 generally provide a non-cognitive feedback. A binaural beat generator provides neurological feedback by providing low resonance frequency sound waves that facilitate the brain's producing the desired patterns. The neural net adjusting the thresholds provides feedback in making the actions easier or harder to assist in training the brain.

Referring now to FIGS. 1 and 3-7, one exemplary embodiment of a therapeutic system 100 capable of performing the methodology 150 described above is provided. Therapeutic system 100 will generally be described in functional block diagrams and the like. One of ordinary skill in the art on reading the disclosure will appreciate that the various illustrative functional blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

Referring first to FIG. 3, the raw electrical signal obtained by sensors 102 is converted to a format usable by computer processors or the like. To convert the raw brainwave signals sensed by sensors 102, brainwave signals 116, 118 are transmitted to a conventional electroencephalogram (EEG) 202, or similar device. The EEG 202 amplifies the electrical signals using amplifier 204 and digitizes the signals using an analog to digital (ADC) 206 to produce amplified, digitized brainwave signals 208, 210. The EEG 202 may be separate as shown or integrated into control processor 104.

Figure 4:
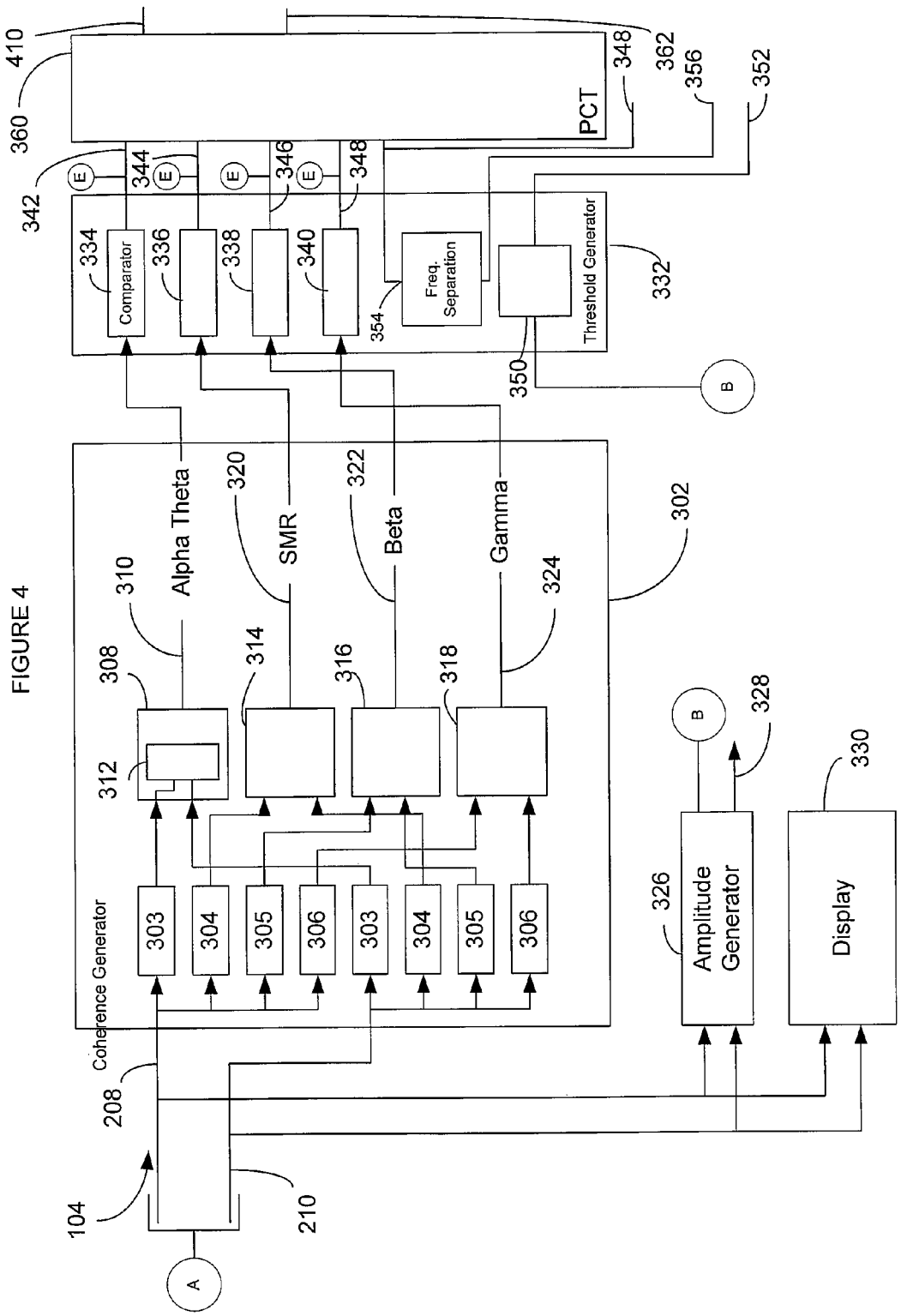
FIG. 4 shows various modules of the control processor of FIG. 1.

The control processor 104 will now be described with reference to the figures. Each of the parts identified in figures may be individual components, integrated into a single component, or integrated into more or fewer components. Referring first to FIG. 4, the amplified, digitized left brainwave signal 208 and the amplified, digitized right brainwave signal 210 are input to a coherence module 302. Coherence module 302 in general provides a coherence value between the two brainwave signals—in this case the left hemisphere brainwave signal and the right hemisphere brainwave signal although any two brainwaves are possible. The coherence module 302 provides coherence for each of the various types of brainwaves. Thus the amplified, digitized brainwave signal 208 is input through a series of band pass filters 303, 304, 305, and 306. More or fewer filters may be used as a matter of design choice depending on what values are to be measured for coherence. As shown, the filters are shown in parallel to provide four distinct outputs for each amplified, digitized brainwave signal 208, 210. The band pass filters 303-306 may be individual filters, a software module, or integrated into a single device, such as a microchip or the like. Filter 303 passes a first frequency band, filter 304 passes a second frequency band, filter 305 passes a third frequency band, and filter 306 passes a fourth frequency band. One exemplary first frequency band may be 6 to 11 Hz. The 6 to 11 Hz comprises Alpha Theta brainwaves. One exemplary second frequency band may be 12 to 15 Hz. The 12 to 15 Hz comprises sensory motor rhythm brainwaves, sometimes referred to as SMR or "low Beta." One exemplary third frequency band may be 18-28 Hz. The 18 to 28 Hz comprises Beta brainwaves. One exemplary fourth frequency band may be 37 to 49 Hz. The 37 to 49 Hz comprises Gamma brainwaves. The exemplary frequency bands shown are smaller than the traditional ranges for the respective brainwaves, for example, the Alpha Theta range is typically considered to extend from about 4 Hz to about 12 Hz. The reduced frequency range of each band, however, allows a frequency separation between the bands. The first exemplary frequency band, may be, for example, 4 to 12 Hz to cover the entire traditional range of the Alpha Theta brainwaves, but perhaps would need to be reduced to provide a clear separation between the frequency bands. While the frequency ranges and number of comparisons is a matter of specific design choice and functionality desired, the technology of the present application will generally be explained with reference to the four frequency ranges provided above recognizing that more, less, and different frequency ranges are possible over the spectrum of brainwave frequencies. The chosen frequency ranges is in part based on current understanding of the brain and its function indicating that in general wellness is increased with increased coherence among Alpha Theta brainwaves and decreased coherence among Beta brainwaves.

Once the frequency signals are separated into one left amplified, digitized first frequency range signal and one right amplified, digitized first frequency range signal, the one left amplified, digitized first frequency range signal and the one right amplified, digitized first frequency signal are input into a first frequency range coherence generator 308. In this case, the first frequency range is the Alpha Theta range. Thus, the first coherence generator 308 is generating an Alpha Theta coherence signal 310. Conventionally, coherence is determined by comparing the values of cross-power spectrum from one wave form to another wave form in the frequency spectrum. Thus, the first coherence generator 308 may include a Fourier transform generator 312, and such a transformation may be completed using, for example, a quadrature filter as is generally known in the art. As this example has been arranged with four frequency ranges, the coherence module 302 includes four coherence generators 308 (as explained above), 314, 316, and 318, which could be separate hardware, software modules, or integrated into single parts. Coherence generators 314, 316, and 318 may similarly include a Fourier transform generator 312 although other types of coherence may be measured instead of power of the waveform. Coherence generator 314, in this example, provides a SMR coherence signal 320. Coherence generator 316, in this example, provides a Beta coherence signal 322. Coherence generator 318, in this example, provides a Gamma coherence signal 324. The designations Alpha Theta coherence, SMR coherence, Beta coherence, and Gamma coherence used herein are for simplicity of reference. The particular frequency ranges selected in this example should not be considered limiting. By way of reference, coherence generally can be considered a value between 0% coherence (or discoherence or out of synch or morphologically dissimilar) to 100% coherence, which indicates identical wave forms.

Amplified, digitized brainwaves 208, 210 also may be combined by an amplitude generator 326 to form a total brainwave amplitude signal 328. While shown separate from coherence module 302, amplitude generator 326 may be integrated with the coherence module 302 as it also uses the amplified, digitized brainwaves directly from EEG 202. The amplified, digitized brainwaves 208 and 210 may be displayed on a display 330, such as a conventional monitor, LCD screen, flat screen, or the like. Displaying the amplified, digitized brainwaves 208 and 210 may indicate whether, for example, an electrode is properly oriented, whether the cables or transmitters are properly connected, or the like.

The coherence signals, Alpha Theta coherence signal 310, SMR coherence signal 320, Beta coherence signal 322, and Gamma coherence signal 324 are transmitted to a threshold module 332 portion of control processor 104. Again, threshold module 332 may be integrated into a single control processor 104 or a separate, networked control processor 104. In this exemplary embodiment, threshold module 332 determines whether particular coherences are, for example, above a certain minimum threshold, below a certain maximum threshold, or between a certain minimum and maximum, and whether they are increasing, are decreasing, or some combination thereof, such as, for example, above a certain minimum threshold and increasing. Generally, threshold module 332 comprises a series of comparators to provide a modified output data stream based on the comparisons made. In one exemplary embodiment, threshold module 332 comprises at least one comparator for each coherence determination. Thus, threshold module 332 may include comparators 334, 336, 338, and 340. In this exemplary embodiment, comparator 334 makes a first threshold determination based on comparing a present Alpha Theta coherence to the previous Alpha Theta coherence. If the comparison indicates coherence is increasing, the comparator outputs an Increasing Alpha Coherence signal 342. If coherence is constant (unlikely) or decreasing, the comparator does not output the Increasing Alpha Coherence signal 342. In this exemplary embodiment, comparator 336 may determine decreasing Beta coherence to output a Decreasing Beta Coherence signal 344. Comparator 338 may determine a SMR Coherence to output an Increasing SMR Coherence signal 346. Finally, comparator 340 may determine a Gamma coherence to output an Increasing Gamma Coherence signal 348.

In one working embodiment of the technology of the present application, a useful threshold calculation includes band ratio determinations. The ratio is calculated by a ratio generator 350 in threshold module 332 that generates at least one first ratio signal 352. First signal 352 may be a ratio caparison of one frequency range to another, for example, the amplitude of the Alpha frequency range divided by the amplitude of the Theta frequency range. Other ratios, more, and different ratios are possible. In this example, the amplitude signals to generate the ratio may be received from amplitude generator 326. The first signal 352 may be used, for example, as a control input, sometimes referred to as an auto threshold. When the first signal 352 exceeds a predefined threshold, a positive or achieved state is output by threshold module 332. The positive or achieve state allows the feedback mechanism, i.e., the auto logic cascade identified above to monitor and adjust threshold values based on predefined satisfactory response criteria. Conversely, when the negative, null, or not achieved state is output by threshold module, the thresholds associated with threshold module 332 are locked. Ratio generator 350 also may output an indication regarding whether the ratio between the ranges is increasing, decreasing, or remaining steady.

As one of ordinary skill in the art would now recognize on reading the disclosure herein, coherence between separate brainwaves changes rapidly and moment to moment. By inputting the coherence signal to compare the signal to a threshold, the rapidly changing brainwave coherence is less problematic for a control signal as the coherence typically tends to increase or decrease at a less rapid rate. Additionally, the threshold determination may be based on a hysteresis, such that, for example, once the threshold is achieved at a first predetermined level, it will not be turned off (or unachieved) until a second predetermined level is reached. Furthermore, the actual threshold values themselves become useful output since they take advantage of the hysteresis inherent in the neural net aspect of this design. Moreover, as can be appreciated by one of ordinary skill in the art on reading the disclosure, increasing Alpha Theta coherence while decreasing Beta coherence is generally considered a good therapeutic result. Thus, the above thresholds are largely based on therapeutic considerations and not necessarily on, for example, game simulations, prosthesis control, or the like. In other words, more, less, different, other, or a combination of these and other threshold determinations are possible depending on the desired output of the system. Other threshold values may include, for example, an Alpha Theta phase synchronization relating to the phase difference between the first and second brainwave signals being measured. Still other threshold values may include, for example, total or individual wave amplitude threshold values. Yet other thresholds may compare relative coherence or discoherence between ranges, such as a ratio between Alpha Theta coherence as compared to Beta coherence. These examples of various thresholds are simply that, and should be considered exemplary and non-limiting examples.

The outputs of threshold module 332 are provided to a perceptual control theory (PCT) processor 360. PCT processor 360 combines the inputs from threshold module 332, coherence module 302, amplitude generator 326, other, less, more, or different inputs as desired into a PCT control output stream 362 usable to a portion of the display, which will be explained further below with regard to FIG. 7. PCT control output stream 362 is generally understood in the art and will not be further explained except as necessary to explain the present invention. As shown in the figure for simplicity, PCT processor 360 is shown as receiving input from threshold module 332 only.

PCT processor 360 can generate a control signal using a number of different calculations relating to the thresholds and coherence values measures as described above. The inputs are processed by the PCT processor 360 to output a video signal as described in conjunction with FIG. 7 below. The video signal is designed to influence brain function to produce the desired brainwave activity. Some exemplary calculations include, equation 1:

(Increasing Alpha Theta Coherence signal 342−Decreasing Beta Coherence signal 344) divided by (Increasing Alpha Theta Coherence signal 342+ Decreasing Beta Coherence signal 344)

This is the equation for Frequency Separation and is the input to threshold 3 (noted below). This is one of the values inserted into the PCT data stream. This equation is not necessarily in and of itself a PCT calculation.

Equation 1 returns a value between −1 and 1. The closer the value to 1 indicates the greater relative difference between Alpha Theta Coherence and Beta Coherence. Increasing Alpha Theta coherence while decreasing Beta Coherence is considered to have a positive therapeutic effect.

The result of equation 1 also is used to generate a Frequency Separation signal 356 by a frequency separation generator 354 in threshold module 332. In particular frequency separation generator 354 produces the frequency separation signal 356 if the result of equation 1 shows increasing dominance of Alpha Theta Coherence over Beta Coherence.

Absolute value of (Increasing Alpha Theta Coherence signal 342−Decreasing Beta Coherence signal 344)     Equation 2

Equation 2 returns an absolute value of the difference between Alpha Theta Coherence and Beta Coherence.

(Increasing Alpha Theta Coherence signal 342−Decreasing Beta Coherence signal 344)*100     Equation 3

(Increasing Alpha Theta Coherence signal 342)*100     Equation 4

(Decreasing Beta Coherence signal 344)*100     Equation 5

The PCT processor 360 further defines a continuous PCT control output stream 362 by selecting the minimum value of 300 or the result of (note the absolute values of each additive is taken in the equation 6 below):

((Increasing Alpha Theta Coherence ratio signal 342−Decreasing Beta Coherence ratio signal 344+frequency separation ratio signal 356+first ratio signal (Alpha/Theta ratio) 352+Increasing SMR Coherence signal 348)*29

The PCT processor 360 may be increased (make control more difficult) or decreased (make control easier) by adjusting the multiplier "29" up or down. Generally the multiplier may be adjusted between about 25 to 33. The control output signal 118 sends a positive value, in the above exemplary embodiment, when the value of equation 6 is greater than 160 and a negative value or "0" when the value of equation 6 is less than 160. Again, the difficultly of control may be modified up or down by adjusting the value up or down from 160. Generally, value 160 may be adjusted between about 145 (easy) to about 175 (hard) to adjust control.

The PCT control output stream 362 provides visual feedback relating to a virtual object as will be explained below. The virtual object provides visual feedback to patient 108.

Figure 5:
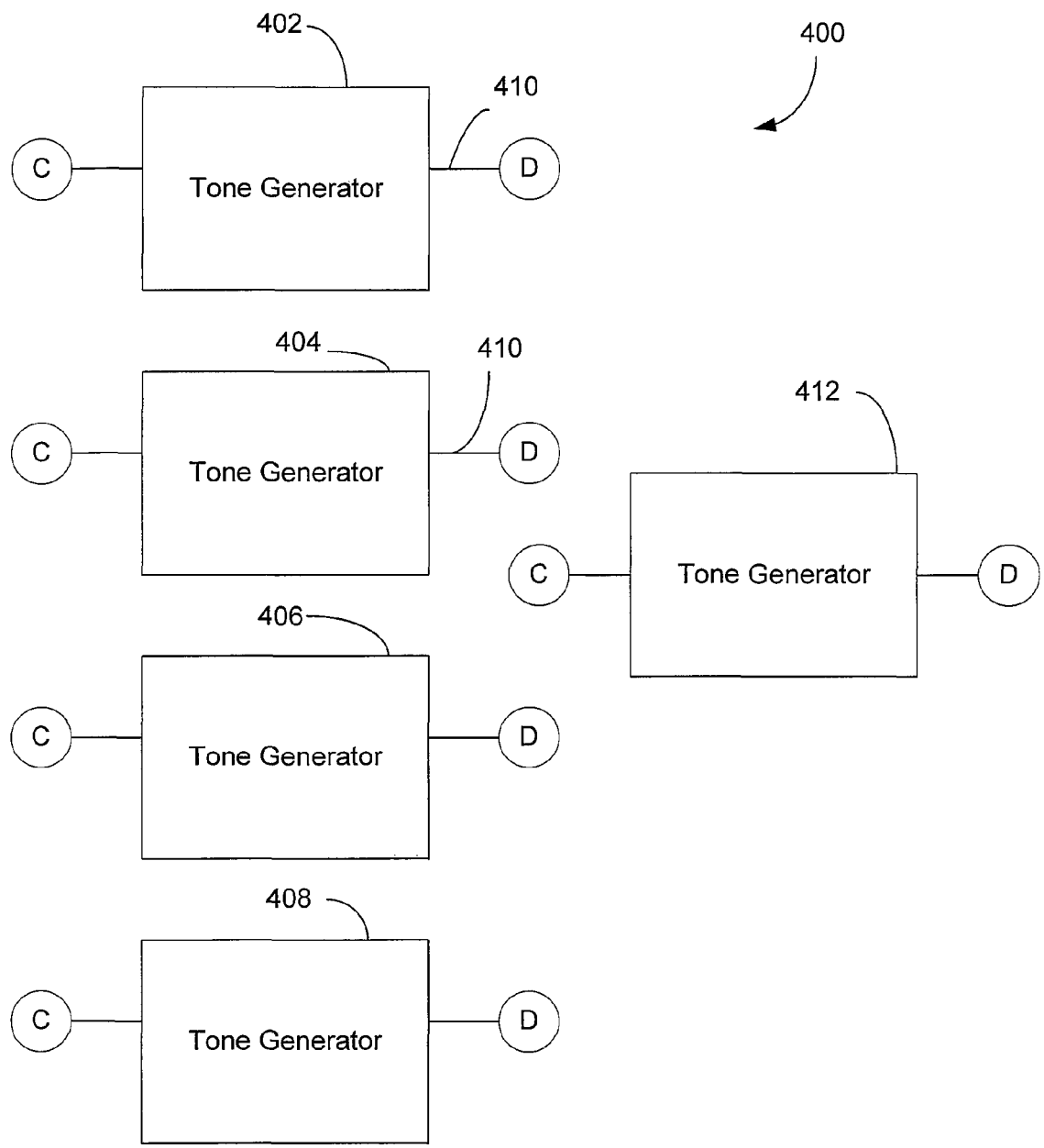
FIG. 5 shows portions of a binaural beat generator of the control processor of FIG. 1.

Another form of feedback provided is a binaural beat, which is a non-cognitive feedback. Referring back to FIG. 1, one or more speakers or tone generators 120 are provided about user 108. FIG. 5 shows a binaural beat generator 400 in more detail. Binaural beat generator 400 includes a plurality of tone generators 402, 404, 406, and 408. The paired tone generators are used to provide interference of a particular binaural beat. In this exemplary embodiment, tone generator 402 provides a 60 Hz signal to, for example, the right ear of user 108 and tone generator 404 provides a 68 Hz signal to, for example, the left ear. The interference of the tone generators 402 and 404 provides a binaural beat frequency of 8 Hz. Tone generator 406 provides a 104.1 Hz signal to, for example, the left ear. Tone generator 408 provides, a 149.1 Hz signal to, for example, the right ear. The interference of the tone generators 406 and 408 provide a binaural beat frequency of 45 Hz. Other binaural beats may be used as desired. The binaural beats produced by binaural beat generator provide an induced resonance frequency causing non-cognitive feedback to the user via the ears, body and head and tend to assist in the formation of the desired brainwave coherence. In this example, tone generators 402, 404, 406, and 408 are activated by a first feedback signal 410 generated by PCT processor 360 indicating that equation 3 is approaching 1. In general, the tones produced by the binaural beat generator 400 may include more or less tones, but producing three tones has been satisfactory for a prototype. The frequencies of the three tones include 6 Hz (Theta), 8 Hz (Low Alpha) & 45 Hz (High Gamma) Each tends to assist improving coherence at or near its own frequency. The 6 & 8 Hz tones are generated when Frequency Separation is decreasing (below threshold). The 45 Hz tone is generated when Frequency Separation is above threshold. Binaural beat generator 400 further includes an audio player 412 providing a 6 Hz signal. The signal using a transfer function to move the sound to provide the illusion of a moving sound source.

Figure 6:
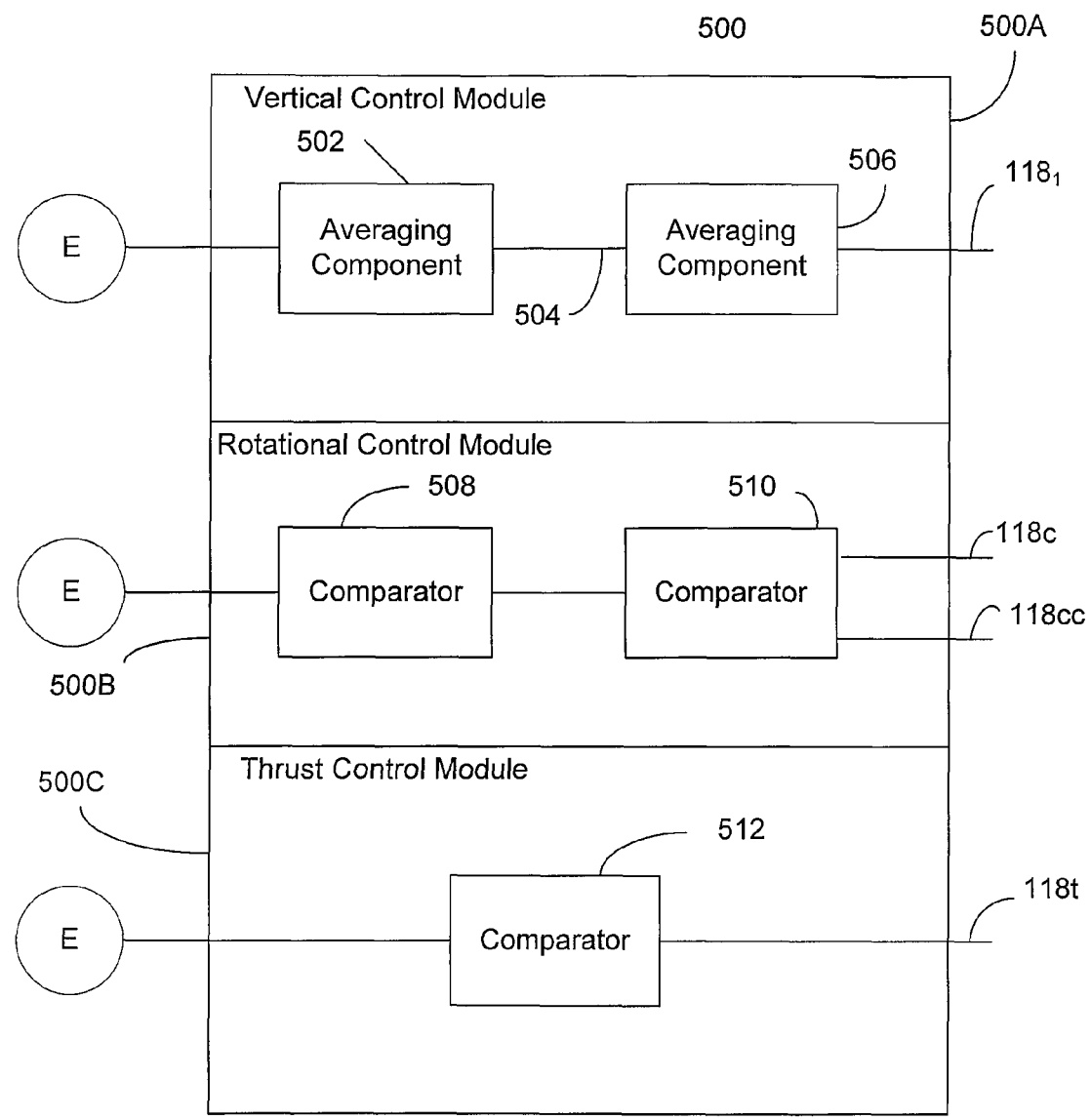
FIG. 6 shows a control module of FIG. 1.

Referring now to FIG. 6 a control module 500 is provided. Control module 500 may be integrated into control processor 104 or a separate unit as a matter of design choice. Control module 500 receives a series of inputs from threshold module 332 and uses those inputs to generate the control output signal 118. Control module 500 is separated into three components to provided three dimensional control signals, which in this exemplary embodiment include a vertical control module 500A, a rotational control module 500B, and a thrust control module 500C. Other control modules to provide three dimensional control signals are possible.

Control module 500 includes vertical control module 500A. Vertical control module 500A includes an averaging component 502. Averaging component 502 receives input indicative of the actual value of the threshold as determined by the neural net over a long and short window, i.e., dynamic averaging. A long window of about 120 seconds and a short window of about 5 seconds provide satisfactory results. Although the above identified windows have proven satisfactory with a prototype, the window was empirically determined to provide the smoothest possible response once again riding the hysteresis latency identified above. The precedent for this type of calculation goes back to the early days of biofeedback when temperature training was accomplished by feeding back only the rate of change information while ignoring absolute values. In this case increasing the degree of improvement provides increased vertical lift. Referring back to FIG. 4, threshold module 332 includes, for example, a comparator 334 that outputs a positive response when it is determined that the Alpha Theta coherence is increasing, i.e., the Increasing Alpha Coherence threshold signal 342. In this exemplary embodiment, control module 500 uses averaging component 502 to average Increasing Alpha Coherence threshold signal 342 over a long window, Decreasing Beta Coherence threshold signal 344 over a long window, Increasing Alpha Coherence threshold signal 342 over a short window, and Decreasing Beta Coherence threshold signal 344 over a short window.

The desired dynamic averaging of threshold signals 504 generated by averaging component 502 are provided to ratio component 506. Ratio component 506 creates a dynamic ratio of ratios by dividing the ratio of the short window moving average by the long window moving average and outputs a first control signal $118_1$ based on the ratios. In this exemplary embodiment, the first control signal is used as a vertical control signal, i.e., lift. The first control signal $118_1$ provides a control value to both a virtual object and a real object in this case to provide lift indication. Anecdotal evidence suggests lift may be the portion of the system most responsive to training. Averaging component 502 and ratio component 506 may be referred to as first or vertical control module 500A.

Control module 500 comprises a second or, in this example, rotational control module 500B. Rotational control module 500B receives first ratio signal 352 from threshold module 332 and uses a first comparator 508 to determine whether the first ratio signal 352 satisfies a first predetermined threshold, either above a minimum, below a maximum, or a combination thereof. In one exemplary embodiment, comparator 508 outputs a high signal on successfully meeting a high threshold value and outputs a low signal on successfully meeting a low threshold value. To maintain separation between vertical and rotational controls, vertical control is based primarily on coherence without amplitude considerations and rotational control is determined on the basis of calculating the amplitude or energy ratios. In the exemplary prototype, Alpha amplitude dominance will produce a clockwise spin control 118c and Theta amplitude dominance will produce a counter-clockwise spin control 118cc. Relative Alpha/Theta balance (not necessarily parity) will stabilize spin. Spin may function by determining the "SPIN" or "NO SPIN" state based on 1) the Alpha/Theta amplitude ratio, 2) the altitude, and 3) if the round is in the first 30-seconds. Otherwise no rotational control signal is output.

Control module 500 includes or comprises a thrust control module 500C. Thrust control in this exemplary embodiment uses one or more comparators 512 to determine whether all the generated coherence signals are above (below) certain minimum threshold values. For example, comparator(s) 512 may determine whether the following signals meet a predetermined minimum coherence level:

Increasing Alpha Theta Coherence signal 342.
Increasing SMR Coherence signal 346.
Increasing Gamma Coherence signal 348.
Decreasing Beta Coherence signal 344.

Based on the combined determination that coherence is above a minimum value and other signals determined from the actual threshold values and combined in a logical statement, thrust control module 500C outputs a thrust control signal $118_T$. For example, if the combined coherence is above a minimum value and it is determined the rotation of the device is zero (i.e., signals $118_c$ and $118_{cc}$ are below values to cause rotational movement), thrust control signal $118_T$ may be positive to provide forward motion of control object 106.

Regarding the controls, the logic cascade described above also provides an output assist/control feature. In particular, the feedback loop may assist or control the ability of the control object, whether virtual or real, to move. For example, the system may first confirm the vertical control module 500A has provided a particular amount of lift as defined by the control signal $118_1$, which amount may vary between 0% lift to 100% lift. Once a predetermined amount of lift is determined or provided, rotation control module is enabled and allowed to provide either clockwise rotation or counter clockwise rotation. If the rotation control is enabled and providing a rotational control signal, i.e., the control object is rotating clockwise or counter clockwise, then thrust control module 500C is disabled. If rotational control module 500B is enabled, but the rotational signal is below a predetermined amount of rotation, which may be set as low as zero rotation or as high as full rotation, the thrust control module 500C is enabled to provide thrust to control object 118 to cause movement through a 3 dimensional space (whether real or virtual).

Figure 7:
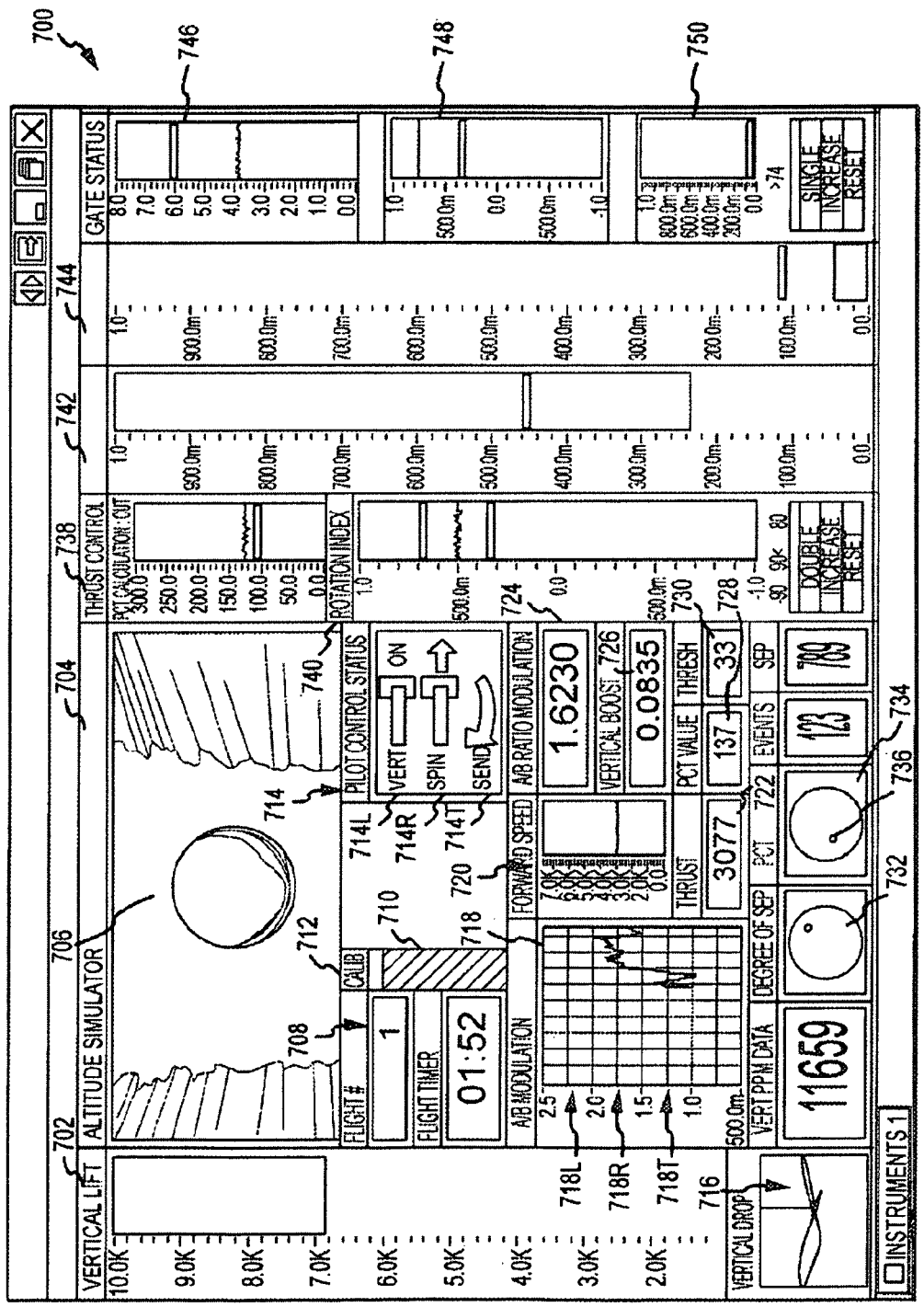
FIG. 7 is an exemplary embodiment of a display of information associated with the technology of the present application.

Referring now to FIG. 7, an exemplary display 700 associated with the therapeutic system 100 is provided. Display 700 is visually shown on displays 119 (FIG. 1, or a display 330 FIG. 4). Display 700 includes a number of displays that assist patient 108 and/or a therapist to facilitate use of therapeutic system 100. For example, display 700 may include a vertical lift display 702 shown as a simple bar graph and an altitude simulator 704. Altitude simulator 704 may display a video representation 706 of the control object 106. Generally, the lift display 702 and altitude simulator 704 may display similar information in different formats relating to the vertical lift of control object 106. In some cases, the video display may assist a patient 108 maintain flight status when they have difficulty controlling the real object. While two formats are shown, other similar displays could be provided. Display 700 also may provide an indicator 708 of the number of times patient 108 has used the therapeutic system 100, which could be the number of times in a single session or the number of times over multiple sessions, as well as a timer display 710, which displays for example the time of a current flight use, the total time of a current session, or a total time across multiple sessions. Display 700 also includes a calibration display 712. The Calibration display measures time during the first 30 seconds of each round during which time all controls are off-line while the computer 1) re-establishes a baseline and 2) initializes one of the drive chips on the UFO receiver. Display 700 further includes a video display 714 of all control object movement control output signals 118 include a display associated with lift 714L, rotation 714R, and thrust 714T, which may correspond to an animation 716 and graph 718. Animation 716 would animate the control signals 714L, 714R, and 714T onto an animation of control object 106. Similarly, graph 718 would show separate traces 718L, 718R, and 718T over time of the control output signals 118. Display 720 is a bar graph associated with forward speed of control object 106. Display 722, 724, 726, 728, and 730 display numerical values associated with each of thrust, power, lift, PCT value and threshold difference. The Threshold Difference Display shows the mathematical difference between the threshold values under consideration. Display 700 also includes a frequency separation video display 732.

PCT video display 734 provides the PCT control output stream 362 to generate indicator 736. PCT control output stream 362 places indicator 736 at a location on display 734 such that patient 108 should attempt to locate indicator 736 using eye contact. By concentrating on moving indicator 736 to the center, for example, of display 734, the patient's brainwaves are influenced in the proper direction.

Display 700 also may include displays related to the various threshold and calculations such as display 738 (thrust control), display 740 (rotation), display 742 (Increase Alpha Theta Coherence), display 744 (Decreases Beta Coherence), display 746 (gate status), display 748 (frequency separation), and display 750 (Increase Gamma Coherence).

One working embodiment of the technology of the present application is provided. This summary is broken down into modules, similar to the above, including modules 1-10. Modules 1, 2 and 3 may be referred to as stage one of the overall technology described above and include converting the raw EEG signal into meaningful data streams. Modules 4, 5, 6, 7, 8, and 9, may be referred to as stage two of the overall technology described above and include encoding the data streams into discreet data usable as biofeedback. Module 10 may be referred to as stage three of the overall technology described above and includes dynamic interaction using the adaptive and self-adjusting calculations as described. Finally, a stage four of the overall technology, not represented by a module, may be described as the output to control a remote device. Moreover, the various algorithms may be considered as the coherence values established in Module One are passed to threshold objects that calculate: 1) pass/fail states modified by input from the neural net, 2) threshold to signal ratios. The neural net described in Module Ten is an adaptive logic cascade that links all the threshold objects together into a dynamic decision making network.

The software algorithms are composed of the following elements:
1. Four coherence bandwidths
2. Coherence frequency separation/dispersion calculation
3. Neural Net linking auto threshold switches into a rational/adaptive decision tree
4. Novel calculation (neurogistic euphonics) of binaural beats frequencies to produce IRF (Induced Resonant Frequencies)
5. Use of IRF as subliminal feedback loop including tactile feedback
6. PCT (Perceptual Control Theory) data streaming
7. Two-branch alternating feedback decision tree
8. Output (Piloting) algorithms (cerebotic response):
   a. RATIO OUTPUT (Vertical): Regression of regressions analysis of Alpha-theta/Beta neural net output
   b. AMPLITUDE BALANCE OUTPUT (Rotational): Simple Alpha/Theta amplitude ratio
   c. DIRECT PCT OUTPUT (Forward thrust): Total of Neural Net control outputs Module I
Inputs & Coherence Calculations Module One receives the two external EEG inputs, filters the signal for noise and performs all initial mathematical transforms. This module is comprised of a total of 13 objects: 2 EEG input devices, 4 filters, 2 spectrum analyzer display objects, 4 coherence objects, and an equation calculation object.

The initial signal processing is the active calculation from the two EEG inputs of coherence for four separate bandwidths: AlphaTheta 6-11 Hz; SMR 12-15 Hz; Beta 18-28 Hz; Gamma 37-49 Hz.

Coherence is dynamically calculated within the BioExplorer software presumably using the outputs of a quadrature filter (90° phase shift converting sine into cosine) inserted into the basic coherence equation identified as the cross-power spectrum divided by the sum of the autospectra.

One definition of the mathematics for coherence was provided by Robert W. Thatcher, Ph.D., et al. in "An EEG Severity Index of Traumatic Brain Injury", J. Neuropsychiatry Clin. Neurosci. 13:77-87, February 2001, "Coherence is defined as $$\Gamma_{xy}^2(f) = \frac{[G_{xy}(f)]^2}{[G_{xx}(f)G_{yy}(f)]}$$

where $G_{xy}(f)$ is the cross-power spectral density and $G_{xx}(f)$ and $G_{yy}(f)$ are the respective autopower spectral densities." "The computational procedure to obtain coherence involved first computing the power spectra for x and y and then computing the normalized cross-spectra. Because complex analyses are involved, this produced the cospectrum (r for real) and quadspectrum (q for imaginary). Then coherence was computed as $$\Gamma_{xy}^2 = \frac{r_{xy}^2 + q_{xy}^2}{G_{xx}G_{yy}}.$$

Further mathematical details of the analyses are provided elsewhere."

The Design Objects of this module are as follows. Input includes Source 1 & Source 2 that receive the raw EEG data via serial, parallel or USB interface through COM1 or data port. Filters provided as Filter 1 & Filter 3 are highpass $6^{th}$ order Butterworth filters and permit frequencies above 1.50 Hz and Filter 2 & Filter 4 are lowpass FIR filters of length 80 and permit frequencies below 56 Hz.

Coherence Calculators are provided. The coherence calculators provide:
Coherence 1 (6-11 Hz, AlphaTheta Up) uses a Chebyshev IIR $3^{rd}$ order filter with a 100.0 m ripple.
Coherence 2 (18-28 Hz, Beta Down) uses a Butterworth IIR $6^{th}$ order filter.
Coherence 3 (12-15 Hz, SMR Up) uses a Butterworth IIR $6^{th}$ order filter.
Coherence 4 (37-49 Hz, Gamma Up) uses a Butterworth IIR $6^{th}$ order filter.

The Calculation Object of Module One is Expression 7 (Band Ratio Calc) which combines the two raw EEG signals by simple addition for later analysis of EEG amplitude ratios.

Visual Display Objects include a Spectrum Analyzer 1 (RHemisphere) & Spectrum Analyzer 2 (LHemisphere) which use Hann filtering with 128 Bins and a refresh rate of 100 ms. The display range is set to record amplitude activity from 2 to 50 Hz with a sensitivity of 20.0 microvolts. These displays provide information used to determine signal strength, electrode status and artifact status in real time.

Module II

Module II includes BASIC THRESHOLD CALCULATIONS. This can be considered one of the primary processors for the incoming coherence data from Module I and establishes the essential calculations on which the rest of the design depends. Module Two is adaptive and is both part of and under the control of the primary neural net configuration (Module Ten).

This module II is comprised of a total of 11 objects: 8 calculation objects and 3 display objects. The calculation objects include 7 threshold calculation devices and one band ratio calculation device. The display objects include 2 bar graph displays and one trend graphic display. The bar graphs are shown in FIG. 7.

Calculation Objects

Threshold 1 (Incr Alpha Coh) receives coherence input from Coherence 1 (AlphaTheta Up) and calculates success based on increase only at a base tolerance of 40%. The auto-threshold function receives control activation from NOT 1 (NOT Sep) described in Module 3.

Threshold 2 (Deer Beta Coh) receives coherence input from Coherence 2 (Beta Down) and calculates success based on decrease only at a base tolerance of 55%. The auto-threshold function receives control activation from the Pass/Fail output of Threshold 4 (Alpha Sync).

Threshold 3 (Freq Sep) receives input from an Expression device (Freq Sep Calc) described in Module 3 and calculates success based on increase only at a base tolerance of 75% with 200 ms averaging. The auto-threshold function receives control activation from the Pass/Fail output of Threshold 1 (Incr Alpha Coh).

Threshold 4 (Alpha Sync) receives input from the Phase Difference output of Coherence 1 and calculates success based on double thresholds at a base tolerance of 63% for both upper and lower limits. The auto-threshold function receives control activation from the Pass/Fail output of Threshold 3 (Freq Sep).

Threshold 5 (A-T Ratio) receives input from the output of BandRatio 1 and calculates success based on double thresholds at a base tolerance of 75% for both upper and lower limits with 500 ms averaging. The auto-threshold function receives control activation from the Pass/Fail output of Threshold 3 (Freq Sep).

Threshold 6 (SMR COH) receives input from Coherence 3 (SMR Up) and calculates success based on increase only at a base tolerance of 60% with no averaging. The auto-threshold function receives control activation from the Pass/Fail output of Threshold 5 (A-T Ratio).

Threshold 7 (Gamma COH) receives input from Coherence 4 (Gamma Up) and calculates success based on increase only at a base tolerance of 75% with no averaging. The auto-threshold function receives control activation from the output of an Expression device described in Module 3 that calculates a fixed threshold of PCT data.

Band Ratio 1 receives input from the Expression device Band Ratio Calc in Module 1 and calculates the power ratio as:

[Amplitude(8.0-10.0 Hz)] divided by [Amplitude(6.0-8.0 Hz)]

with a resolution of 1 Hz. Output from this device goes to both Threshold 5 (A-T Ratio) and Threshold 9 (Rotation Index: A/T Ratio).

The display objects from the above include a bar graph of (Incr Alpha Coh) displays the signal output from Threshold 1 (Incr Alpha Coh) with no averaging and a 35 ms refresh rate in a range of 0-1 and a bar graph of (Decr Beta Coh) displays the signal output from Threshold 2 (Decr Beta Coh) with no averaging and a 35 ms refresh rate in a range of 0-1.

A trend is provided as (Alpha Coh Dom) combines the coherence outputs of Coherence 1 and Coherence 2. Coherence 1 appears in red as a solid area, and Coherence 2 appears as the background color. In this manner the only data represented will be when Coherence 1 exceeds the value of Coherence 2. The coherence output of Threshold 6 is also represented as a simple line graph. Averaging is 10 secs with a display range of 30 minutes and 300 second delineations to identify each 5-minute period.

Module III

Module III provides calculations for band ratio, frequency separation, PCT, and an AND gate. Module Three creates the three data streams on which the neurofeedback and the pilot controls are based. This module completes Stage One.

This module III is comprised of a total of 16 objects: 9 calculation objects, a Boolean NOT gate, a Boolean OR gate and 5 display objects. The calculation objects include 8 equation devices and one threshold device. The display objects include 2 trend graphic displays and 3 numeric readouts.

Calculation Objects Include:

Threshold 8 (GATE STATUS) receives input from Expression 14 (GATE) and calculates success based on increase only above a threshold with a fixed value of 7. The pass/fail output is used as a limiting factor in Expression 43 (Low Power Assist), controls the auto-threshold function of Threshold 9 and triggers Continuous MIDI 1 (Event Bell). The auto-threshold input function is not used.

Expression 1 (FreqSepCalc) receives inputs from the coherence outputs of Coherence 1 (In1) and Coherence 2 (In2) and processes these data as follows:

(AlphaTheta Coherence−Beta Coherence) divided by (AlphaTheta Coherence+Beta Coherence)

A value in the range of −1 to +1 is returned with the higher value indicating a greater relative difference between Alpha-Theta coherence and Beta Coherence.

Expression 3 receives threshold data from Threshold 4 (AlphaSync) with the low threshold values going to In2 and the high threshold values going to In1. The equation, ABS(In1−In2)

returns the absolute value of the difference between the two thresholds and sends this information to numeric readout Meter 6 (AlphaSyncDiff).

Expression 4 receives data from the low threshold outputs of Threshold 1 (In1) and Threshold 2 (In2) and processes the data through the equation:

(In1−In2)*100 (NOTE: *=multiply)

which is then sent to both numeric (Meter 7, Sep Value) and graphic readouts (Trend 1, DEG of SEP).

Expression 5 receives data from the low threshold outputs of Threshold 1 (In1), multiplies it by 100 and sends these data to Trend 1 (DEG of SEP).

Expression 6 receives data from the low threshold outputs of Threshold 2 (In1), and multiplies it by 100 and sends these data to Trend 1 (DEG of SEP).

Expression 8 (PCT Calculation) receives input from the ratio output of 5 threshold objects to create a continuous data stream. The ratio output is calculated as "the signal divided by the threshold value."

In1 is from Threshold 1.
In2 is from Threshold 2.
In3 is from Threshold 3.
In4 is from Threshold 5.
In5 is from Threshold 6.

Because Threshold 5 uses double thresholds as limits, the ratio output from Threshold 5 is calculated as:

"(the signal minus the low threshold value) divided by (the high threshold value minus the low threshold value)."

The PCT equation is embedded in a logical statement:

MIN(ABS(In1+In2+In3+In4+In5)*29), 300)

and returns the lower value of EITHER the absolute value of the sum of all 5 ratio inputs multiplied by a correction constant with a value of "29" OR "300".

NOTE: The perceived difficulty for the control of the PCT data stream can be adjusted by increasing (easier) or decreasing (harder) the value of the constant through a range of 25 through 33. The effect of this change on the overall design will be slight. These PCT adjustments in Expressions 8, 9 & 29 are the only independent adjustments that can be made in the design. Attempting to change other variables will imbalance the outputs.

Expression 9 receives the PCT data stream from Expression 8 (PCT Calculation). It sends a positive value ("1") when the PCT data stream exceeds a value of 160 and a negative value ("0") when the PCT data stream is 160 or less. The perceived difficulty for the control of the PCT data stream can be adjusted by increasing (harder) or decreasing (easier) the constant value through a range of 145 through 175. The effect of this change on the overall design will be slight. These PCT adjustments in Expressions 8, 9 & 29 are the only independent adjustments that can be made in the design. Attempting to change other variables will imbalance the outputs.

Expression 14 (GATE) receives pass/fail binary data from 8 sources as follows:

In1=Threshold 1
In2=Threshold 2
In3=Threshold 3
In4=Threshold 4

In5=Threshold 5
In6=Threshold 6
In7=Expression 9
In8=Threshold 7
It processes these data by simple addition and sends out a value with a range of 0 to 8.

Also provided in this module three are Boolean operators as follows:

NOT 1 (NOT Sep) receives the pass/fail output from Threshold 3 (FreqSep), reverses it and sends it to OR 2 (NN ON) as well as Tone Generator 1, Tone Generator 2 and Audio Player 1 which are described in Module 4.

OR 2 (NN ON) receives the outputs from NOT 1 (NOT Sep) and Expression 43 (Low Power Assist) and, if either input is not "0", sends an activation signal to the auto-threshold input of Threshold 1 which initiates the neural net cascade.

The display objects include meter 5 (SEP %) displays the output from Expression 1 (FreqSepCalc) in integer only percentage format with a 300.0 ms refresh rate and 2 sec averaging, meter 6 (AlphaSyncDiff) displays the output from Expression 3 as whole integers representing the difference between the high and low threshold values of Threshold 4. There is a 35.0 ms refresh rate with no averaging, and meter 7 (Sep Value) displays the output from Expression 5 as whole integers representing the difference between the low threshold values of Threshold 1 minus Threshold 2. There is a 35.0 ms refresh rate with no averaging, which are all represented in FIG. 7. Also provided is a trend (DEG of SEP) that combines the outputs of Expression 5 and Expression 6. Expression 4 appears in green as a solid area, and Expression 5 appears as the background color (black). In this manner the only data represented will be when Expression 4 exceeds the value of Expression 5. The output of Expression 4 is also represented as a simple line graph (red). Averaging is 10 secs with a display range of 30 minutes and 300-second delineations to identify each 5-minute period. Trend 3 (PCT) displays the output of Expression 8 (PCT Calculation) in graphic format as a line graph. Averaging is 1 sec with a display range of 30 minutes and 300-second delineations to identify each 5-minute period.

Module IV

Module Four is the beginning of Stage Two. It is comprised of 5 objects and is responsible for the neurogistic euphonies which is the non-cognitive portion of the cerebotic link and is responsive to the output of Threshold 3 (Freq Sep). As dispersion of the coherence spectra improves above the dynamic threshold, the 45-Hz binaural beat generator (Tone Generator 3 & Tone Generator 4) is activated providing support with a gamma frequency assist. As dispersion of the coherence spectra drops below the dynamic threshold, the 8-Hz binaural beat generator (Tone Generator 1 & Tone Generator 2) and the 6 Hz HRTF recoding (Audio Player 1) are activated providing assistance for low alpha-theta coherence values.

The frequency of the compatible carrier wave pairs ($W_F$) for beat frequencies ($F_1$, $F_2$) is calculated as follows:

$$W_{F1} = (F)^2 / \{Int[1+(F/10)]\} + (F/2)$$

$$W_{F2} = (F)^2 / \{Int[1+(F/10)]\} - (F/2)$$

Tone Generator 1 (Right Ear 60) emits a sine wave at 60 Hz at 70% volume into the right channel only. This tone is enabled by a pass signal from NOT 1 (NOT Sep). When combined with the output of Tone Generator 2 (Left 68) a binaural beat frequency of 8 Hz is formed midway between the output locations which acts as an IRF in the neurofeedback design.

Tone Generator 2 (Left 68) emits a sine wave at 68 Hz at 70% volume into the left channel only. This tone is enabled by a pass signal from NOT 1 (NOT Sep). When combined with the output of Tone Generator 1 (Right Ear 60) a binaural beat frequency of 8 Hz is formed midway between the output locations which acts as an IRF in the neurofeedback design.

Tone Generator 3 (Left 104.1) emits a sine wave at 104.1 Hz at 95% volume into the left channel only. This tone is enabled by a pass signal from Threshold 3 (Freq Sep). When combined with the output of Tone Generator 4 (Right 149.1) a binaural beat frequency of 45 Hz is formed midway between the output locations which acts as an IRF in the neurofeedback design.

Tone Generator 4 (Right 149.1) emits a sine wave at 149.1 Hz at 95% volume into the left channel only. This tone is enabled by a pass signal from Threshold 3 (Freq Sep). When combined with the output of Tone Generator 4 (Left 104.1) a binaural beat frequency of 45 Hz is formed midway between the output locations which acts as an IRF in the neurofeedback design.

Audio Player 1 (6 Hz HRTF) plays a digitally recorded binaural beat pattern that outputs a 6-Hz pulse with a head related transfer function (HRTF) creating the illusion of a moving sound source. This recording is enabled by a pass signal from NOT 1 (NOT Sep). Volume is set to 100%. The file is "6 Hz hrtf++.wav."

Module V

Module Five manages all temporal aspects of the design: timing and identifying each five-minute round, the 30-second control delay at the start of each round, and maintaining the high count of successful events. This module is comprised of a total of 25 objects: 4 equation calculation objects, 6 counter objects, 2 sample & hold objects, 1 NOT gate, 1 OR gate and 10 display objects. The 10 display objects include 8 numeric readouts, one bar graph and one continuous MIDI generator. This module is controlled by the output of the OR 1 gate.

Calculation Objects Include:

Expression 2 (In1+1) receives the count output of Counter 3 (Period Counter). By adding "1" the final output value starts at "0+1=1".

Expression 22 (Start Delay) receives the outputs from Counter 2 (Period Timer) (In1) and Average 5 (In2).

If((In1<30), 18000, In2)

IF In1 is less than 30 secs THEN send out the value of 18000 (PPM value to arrest vertical lift capability) ELSE send out the value of In2 to control vertical lift (Module 7).

Expression 36 (VerticalDisplayControl) receives the output from Counter 2 (Period Timer) and Expression 29 (High Value Compressor), sends a start signal to the Time High element of Counter 8 (LOFT) and signals initiation of Video Player 4 (Vertical Prop) and MIDI 1 (Lift Tone).

Expression 37 (Reverse Timer) receives the count output from Counter 2 (Period Timer), subtracts this value from 301 and sends the output to Meter 12 (Flight Time).

Boolean Operators Include:

OR 1 (Timer Control) receives the output of the 2 raw EEG signals to activate a timing routine.

NOT 4 receives the delay control output from Expression 35 (FlightStartRecord), reverses it, and sends the output to the reset element of Score 1 (F CTRL/FLT) (Module 9).

Counter Objects Include:

Counter 1 (HIGH) receives the output from Threshold 8 (GATE STATUS) and maintains a cumulative count of all events (Rising Edge) each time a positive ("1") signal is received. These events are defined by Threshold 8 as "7 or 8 positive inputs to the GATE (Expression 14)"

and are cumulative for the entire session regardless of individual period status.

Counter 2 (Period Timer) maintains the time (Time High) for each 300-second period with the end-of-period reset pulse coming from Counter 3 (Period Counter).

Counter 3 (Period Counter) receives the trigger pulse output from Counter 2 (Period Timer) and sends a trigger pulse and cumulative count value at the end of each 300-second period as determined by Counter 2 (Period Timer).

Counter 4 receives the output from Threshold 8 (GATE STATUS) and maintains a cumulative count of all events (Rising Edge) each time a positive ("1") signal is received. This value is reset to "0" when an end-of-period trigger pulse is received from Counter 3 (Period Counter) which then provides a count of events for each period.

Counter 7 (FRWD Count) receives the signal from Expression 15 (FRWD Flight Record) into its "rising edge" element and sends a trigger pulse to Score 2 (FULL CONTROL TTL) once for every 3 inputs.

Counter 8 (LOFT) receives the output from Expression 36 (VerticalDisplayControl) and sends the value representing the total duration of all positive value signals to Expression 42 (LoftCalc).

Sample/Hold Object Include:

Sample/Hold 1 receives the output from Counter 4 as well as the end-of-period trigger pulse from Counter 3 (Period Counter). At the end of each period it will maintain the former period's event total for 15 seconds (Dwell) after the next period starts.

Sample/Hold 2 receives the trigger output from Counter 7 (FRWD Count) and a Hold command from Expression 35 and sends a trigger output to Score 1. The Hold command freezes the output during the 30-second calibrations.

Numeric Display Objects Include:

Meter 1 (High Count) displays the output from Counter 1 (HIGH) as whole integers. There is a 35.0 ms refresh rate with no averaging.

Meter 2 (PERIOD #) displays the output from Expression 2 as whole integers. There is a 35.0 ms refresh rate with no averaging.

Meter 3 (Period Time) displays the output from Counter 2 (Period Timer) to one decimal place in standard time format. There is a 35.0 ms refresh rate with no averaging.

Meter 4 (Period Score) displays the output from Sample/Hold 1 as whole integers. There is a 35.0 ms refresh rate with no averaging.

Meter 10 (GATE EVENTS TTL) displays the output from Counter 1 (HIGH) as whole integers on the Pilot Control Screen. There is a 35.0 ms refresh rate with no averaging.

Meter 12 (Flight Time) displays the output from Expression 37 (Reverse Timer) as a countdown timer on the Pilot Control Screen with no decimals in standard time format. There is a 35.0 ms refresh rate with no averaging.

Meter 14 (PCT Value) displays the output from PCT Calculation (Expression 8) as whole integers on the Pilot Control Screen. There is a 35.0 ms refresh rate with 500 ms averaging.

Meter 15 (Flight #) displays the output from Expression 2 as whole integers on the Pilot Control Screen. There is a 35.0 ms refresh rate with no averaging.

Bar Graph Display Include:

Bar Graph 4 (Calibration) displays the first 30 seconds of each period from Counter 2 (Period Timer) with no averaging and a 35.0 ms refresh rate. Control of the UFO/blimp is withheld during these 30 seconds.

Continuous Midi Generator includes Continuous MIDI 1 (Event Bell) provides a soft bell tone (MIDI Note Value=55; Volume=30) for each event as defined by Threshold 8 (Gate Status).

Module VI

Module Six is responsible for calculating and maintaining an alternating audio/visual feedback display of the primary data streams as secondary pilot control. The outputs of Module Six are used by the pilot/trainee as baseline guides if subjective loss of control is experienced. This module is comprised of a total of 10 objects: 4 equation objects, 2 counter objects, 2 Boolean NOT gates and 2 video players.

Calculation Objects Include:

Expression 10 (In1<6) receives the output of Counter 5 (SEP/DRIVE) and sends out a positive value ("1") until the separation calculation has maintained its target value for a total of 6 seconds.

Expression 11 (In1>6) receives the output of Counter 6 (PCT/ASTROG) and sends out a negative value ("0") until the PCT calculation has met its target value for a total of 6 seconds.

Expression 12 (If(In1=1), 1, 0) receives the output of Expression 10 and relays the pass/fail data to NOT 2.

Expression 13 (If(In1=1), In2, 0) receives the output of Expression 10 as In1 and Threshold 3 (FreqSep) as In2. This enables the audio/visual displays of Degree of Separation.

Counter Objects Include:

Counter 5 (SEP/DRIVE) receives the pass/fail output of Threshold 3 (Freq Sep) and accumulates the pass time which is sent to Expression 10. The value is reset when the condition of Expression 11 is positive.

Counter 6 (PCT/ASTROG) receives the pass/fail data of Expression 9 and accumulates the pass time which is sent to Expression 11. The value is reset when the condition of NOT 3 is negative.

Boolean Operators Include:

NOT 2 receives the pass/fail data from Expression 12, reverses it and sends this signal as activation for the audio/visual displays of PCT. This has the effect of activating the PCT displays only when the Frequency Separation condition has been met.

NOT 3 receives the pass/fail data from Expression 10, reverses it and sends it to reset Counter 6. This has the effect of resetting the PCT display counter when the Frequency Separation condition is met.

Video Players Include:

Video Player 1 (Degree of Sep) receives signal output data from Threshold 3 (FreqSep) and enable control data from Expression 13. The proportional position of the video display responds to a range of −500 m to +500 m with averaging of 500 ms. The video file is "UFO Radar.avi".

Video Player 2 (PCT) receives signal output data from Expression 8 (PCT Calculation) and enable control data from NOT 2. The proportional position of the video display responds to a range of 0 to 300 with averaging of 500 ms. The video file is "UFO Radar.avi".

Module VII

Module Seven is responsible for converting the neural net adjusted threshold values from Module Two into a rational data stream that is further converted into PPM instructions to control the speed of the vertical propeller (or other primary control output) while simultaneously providing audio-visual feedback to the pilot/trainee. This is the primary learning algorithm and, in conjunction with the feedback information from Modules Four, Five and Six, creates the learning environment for enhanced cognitive functioning. The use of the "ratio of ratios" or "regression of regressions" equation in Expression 18 combined with the adaptive quality of the neural nets allows this software design to adjust itself to the training requirements of each individual. This module comprises 29 objects: 5 average calculators, 10 equation objects and 14 display objects. The 14 display objects include: 5 numeric readouts, 3 video players, 1 graphic trend display, 4 bar graph displays and 1 MIDI player.

Average Calculators Include:

Average 1 (Alpha THRESH) receives output from the low threshold value of Threshold 1 (Incr Alpha Coh) and creates a dynamic average across a 120-second moving period.

Average 2 (Beta THRESH) receives output from the low threshold value of Threshold 2 (Decr Beta Coh) and creates a dynamic average across a 120-second moving period.

Average 3 (Alpha Thresh) receives output from the low threshold value of Threshold 1 (Incr Alpha Coh) and creates a dynamic average across a 5-second moving period.

Average 4 (Beta Thresh) receives output from the low threshold value of Threshold 2 (Decr Beta Coh) and creates a dynamic average across a 5-second moving period.

Average 5 receives output from Expression 17 (Ratio PPM) and creates a dynamic average across a 1-second moving period.

The Calculation Objects Include:

Expression 17 (Ratio to PPM) receives the output from Expression 29 (High Value Compressor) and processes it through this logical statement:

$$CEIL(MAX(MIN(((9000-((In1-1)*8000))+8500), 18000), 9000))$$

SUBTRACT "1" from the current ratio value (In 1) and MULTIPLY the result by the PPM constant ("8000"). ADD this resultant to "8500" THEN SUBTRACT the new value from "9000". IF this number is less than "18,000" AND greater than "9000" THEN truncate it to an integer and pass it into the data stream ELSE IF number is greater than "18,000" THEN pass "18,000" into the data stream ELSE IF number is less than "9000" THEN pass "9000" into the data stream.

This expression converts the ratio data into the PPM language used by the RF transmitter and restricts output to the range: 18,000 to 9000. The value of 18,000 is both the lower limit and the null signal, and the value of 9000 is the higher limit. Decreasing the PPM constant (the number after the asterisk) will extend the usable ratio range but will also decrease vertical responsiveness. Usable ratio range: 0.95-2.07.

Expression 18 (A/B COH RATIOS) creates a dynamic ratio of ratios (regression of regressions) by dividing the ratio of the short period moving average of the threshold values of the alpha-theta and beta threshold objects by the ratio of the long period moving average of the threshold values of the alpha-theta and beta threshold objects. To this ratio a threshold correction term from Expression 19 (ADJ THRESH MEAN DIFF) is added (Vertical Boost). This value is multiplied by 100, truncated to integer form (CEIL) and returned to its original magnitude:

$$(CEIL(((In1/In2)/(In3/In4)+In5)*100)/100)$$

This value represents the RATIO OUTPUT which is used as the vertical control data stream in this design. This data stream is sent to Expression 29 (High Value Compressor) before being incorporated into all calculations for output control that follow.

Data input is received as follows:
In1=Average 3 (Alpha Thresh, 5.0 sec)
In2=Average 4 (Beta Thresh, 5.0 sec)
In3=Average 1 (Alpha THRESH, 120.0 sec)
In4=Average 2 (Beta THRESH, 120.0 sec)
In5=Expression 19 (ADJ THRESH MEAN DIFF)
In6=Expression 43 (LOW POWER ASSIST)

Expression 19 (ADJ THRESH MEAN DIFF) receives the outputs from Average 1 (In1) and Average 2 (In2) and processes them through this logical statement:

$$MAX(((In1-In2)/3), 0)$$

This expression creates a correction term that cannot drop below "0" that is sent to Expression 18 (AB COH RATIOS) and Meter 13 (VERTICAL BOOST) and provides a small proportional improvement for vertical responsiveness when the alpha coherence thresholds are greater than the beta coherence thresholds.

Expression 21 (MIN((18000−In1), 8000)) reverses the signal from Expression 22 (Module 5: Start Delay) and sends it to the audio-visual elements. This re-reversal keeps the up and down orientation normalized since the PPM data decreases from 18,000 to 8500 as the vertical lift increases.

Expression 29 (HIGH VALUE COMPRESSOR) modifies the data stream from Expression 18 (A/B COH RATIOS) with the following logical statement:

$$If(In1>1.2, (((In1-1.2)*0.32)+1.2), In1)$$

IF flight altitude exceeds mid-level THEN correct all data beyond that point to 32% of the input values. This statement has the effect of reducing overall lift beyond mid-altitude to allow for a more stable range of data by decreasing the degree of vertical movement in the upper vertical range. Increasing 1.2 will delay the EFFECT of the compression. Increasing 0.32 will diminish the DEGREE of compression. These data are then sent to the following devices: Expression 16 (Forward Base Value), Expression 17 (Ratio to PPM), Expression 24 (ROTATION CALC), Expression 28 (Vertical Control State), Expression 30 (PilotControlStatus), Expression 36 (VerticalDisplayControl), Expression 39 (FlightMeterControl), Expression 43 (LOW POWER ASSIST), Meter 11 (POWER), Meter 16 (POWER OUTPUT) and Trend 4 (FLIGHT RECORD).

Expression 38 (Blue Line) receives the output from Expression 30 and sends a continuous signal with a value of "1" to Ch3 of Trend 4 which has the effect of placing a blue line at "1.0" on the Flight Record.

Expression 39 (FlightMeterControl) receives the output from Expression 29 and uses the following logical statement:

$$MIN(2, In1)$$

This has the effect of limiting the output of this Expression to no more than "2". This output goes to the Position input of Video Player 7 (Flight Meter).

Expression 42 (Loft Calc) receives input from Counter 8 and Expression 2 and uses the following logical statement:

$$MIN(In1/(Time-(In2*30))), 1)$$

This calculates the running ratio of the amount of time the basic flight ratio is above 0.99 against the total running time excluding the calibration periods. This value is sent to Expression 44 (NN Control), Bar Graphs 7 & 8, and Meter 17.

Expression 43 (Low Power Assist) receives the outputs from Expression 44 (NN Control), Expression 29 and Threshold 8 and processes these data through the logical statement:

$$If(((In1=0)\&(In2=1)\&(In3<1.15)), 2.5, 0)$$

IF LOFT % is low (<0.6) AND GATE STATUS is low (<7) AND POWER RATIO is below 1.15 THEN provide power assist of 2.5% to Expression 18 ELSE send a null value, "0".

Expression 44 (NN Control) (Neural Net Control) receives the output signal from Expression 42 (Loft Calc). IF this signal's value drops below 0.6, THEN a value of "1" is sent out to Input 1 of Expression 43 (Low Power Assist) ELSE a null value, "0", is sent.

Numeric Display Objects Include:

Meter 9 (VERT PPM DATA) receives the output from Expression 22 (Start Delay) and reports in integer format the PPM data calculated in Expression 17 (Ratio PPM). Averaging is 500 ms with a 35 ms refresh rate.

Meter 11 (POWER) receives the output from Expression 29 (High Value Compressor) and presents it on the Pilot Control Screen accurate to three decimal places. There is a 35 ms refresh rate with no averaging.

Meter 13 (V BOOST) receives the output from Expression 19 (ADJ THRESH MEAN DIFF) and presents it accurate to four decimal places. There is a 35 ms refresh rate with no averaging.

Meter 16 (POWER OUTPUT) receives the output from Expression 29 (High Value Compressor) and presents it on the Instrument screen accurate to four decimal places. There is a 35 ms refresh rate with no averaging.

Meter 17 (LOFT %) receives the output from Expression 29 (High Value Compressor) and presents it on the Instrument screen accurate to four decimal places. There is a 35 ms refresh rate with no averaging.

The Video Players Include:

Video Player 3 (ALTITUDE SIMULATOR) receives the output from Expression 21 which controls a video representation of the relative vertical position of the control object. The proportional position of the video image responds to an input range of 1 to 9,000 with no averaging. The video file is "TubeRise.avi".

Video Player 4 (VERTICAL PROP) receives the pass/fail output from Expression 36 and presents a video representation of a propeller which is synchronized to be activated when the vertical propeller of the control object is activated. There is no averaging. The video file is "VertProp408.avi".

Video Player 7 (Flight Meter) receives the output from Expression 39 into its Position input and presents an image of a needle meter with special markings to assist data interpretation. The position and movement of the needle is proportional to the fully processed ratio signal. The input range is set to "0-1.9" with 1.0 second averaging. The video file is "FlightMeterB.avi".

Graphic Trend Display Include:

Trend 4 (FLIGHT RECORD) receives the output from Expression 29 (High Value Compressor), Expression 15 (FRWD Flight Record), Expression 35 (Flight Start Record) and Expression 38 (Blue Line) and presents the graphic output on the Pilot Control Screen as a history of vertical and forward flight activity for each 5-minute period. There are horizontal divisions of 30 secs with a vertical axis display range of 0.5 to 2.5 and 1.0 sec averaging.

Bar Graph Displays Include:

Bar Graph 3 (LPA) receives the output from Expression 43 (Low Power Assist) and acts as a signal indicator by changing color completely when the Low Power Assist conditions have been met. There is a 35 ms refresh rate and no averaging.

Bar Graph 6 (V Boost On) receives the output from Expression 19 and acts as a signal indicator by changing color completely when the Adjusted Mean Threshold Difference conditions have been met. There is a 35 ms refresh rate and no averaging.

Bar Graph 7 (PREP) receives the output from Expression 42 (Loft Calc) and presents the data in the range of 0-0.50. There is no averaging and a 35 ms refresh rate.

Bar Graph 8 (OPTIMIZE) receives the output from Expression 42 (Loft Calc) and presents the data in the range of 0.50-1.0. There is a 35 ms refresh rate and no averaging.

MIDI Player Include:

MIDI 1 (Lift Tone) receives the output from Expression 21 for note pitch value and Expression 36 as the enabling signal. Input range is 0 to 8,000 and MIDI note range is 40 to 100. The notes are set to follow a pentatonic major "A" scale at a volume of 40% with no averaging. The MIDI player is set to produce no sound until activated.

Module VIII

Module Eight receives the output of BandRatio 1 (Module Two) and creates a triple state directional control output that can be proportional or state dependent. This parameter is the secondary pilot control. This module comprises of 8 objects which include 4 expression calculations, 1 threshold calculator and 3 display objects.

Threshold Calculator Includes:

Threshold 9 (Rotation Index: A/T Ratio) receives the output from BandRatio 1 (Module Two) and sets upper and lower limits at a base tolerance of 90% success and 1 sec averaging. The auto-threshold function is controlled by the pass/fail output from Threshold 8.

Calculation Objects Include:

Expression 20 (RIGHT Rotation Threshold) receives both the signal output and the high threshold value from Threshold 9 (Rotation Index: A/T Ratio). IF the signal (In1) is greater than the threshold (In2) THEN the value "15,000" is sent to Expression 24 (ROTATION CALC) to initiate a right (clockwise) spin. IF the signal is less than the threshold THEN a null value is sent.

Expression 23 (LEFT Rotation Threshold) receives both the signal output and the low threshold value from Threshold 9 (Rotation Index: A/T Ratio). IF the signal (In1) is less than the threshold (In2) THEN the value "20,000" is sent to Expression 24 (ROTATION CALC) to initiate a left (counterclockwise) spin. IF the signal is greater than the threshold THEN a null value is sent.

Expression 24 (ROTATION CALC) receives outputs from Expression 29 (High Value Compressor) (In3), Expression 20 (RIGHT Rotation Threshold) (In1), Expression 23 (LEFT Rotation Threshold) (In2) and Counter 2 (Period Timer) (In4) and calculates the AMPLITUDE BALANCE OUTPUT by processing these data through the following logical statement:

$$If(((In1+In2)=0)|(In3<1.2)|(In4<31), 18000, (In1+In2))$$

IF both rotation values are null OR IF the altitude is too low OR IF the timer is in the 30-second calibration phase THEN a value of "18,000" is sent to In1 of Server 1 (LINK to RF TRANS) which will arrest rotational action ELSE the sum of In1+In2 will send appropriate rotational instructions.

Expression 40 (Spin Meter Control) receives output from Expression 30 (PilotControlStatus) and instructs Video Player 6 to engage the Spin video only when spin is possible.

$$If((In1>29), In1, 0)$$

Display Objects Include:

Bar Graph 5 (Stabilization) receives data from the Pass % output of Threshold 5 (A-T Ratio) and presents information within a range of 0.46-0.51 with 10 second averaging and a 35-ms refresh rate.

Meter 8 (Stabilization) receives data from the Pass % output of Threshold 5 (A-T Ratio) and presents numeric information to 3 decimal places with 10 second averaging and a 35-ms refresh rate.

Video Player 6 (SPIN) receives Position data from the Ratio output of Threshold 9 and Enable instructions from Expression 40. The video file is "UFO Spin E5f.avi", and there is 2-second averaging.

Module IX

Module 9 is responsible for pilot control status displays, control of forward thrust as the third control parameter and connection to the Server object which provides the data output link to the PPM software which will ultimately be controlling the radio transmitter. This module comprises of 22 objects: 13 equation calculations, 1 threshold calculator, 1 numeric display, 3 video players, 2 score devices, 1 audio player and 1 server object.

The Calculation Objects Include:

Expression 15 (FRWD Flight Record) receives input from Expression 30 (PILOT CONTROL STATUS) and determines when forward flight has been activated.

If((In1=56), 0.75, 0)

IF forward flight has been approved by Expression 30 (PILOT CONTROL STATUS) THEN direct Channel 2 of Trend 4 (FLIGHT RECORD) to place a small yellow bar on the Flight Record screen.

Expression 16 (FORWARD Base Value) calculates the DIRECT PCT OUTPUT which is used as forward thrust in this design and receives the outputs from 8 sources:

In1=low threshold value of Threshold 1 (Incr Alpha Coh)
In2=low threshold value of Threshold 2 (Decr Beta Coh)
In3=low threshold value of Threshold 6 (SMR COH)
In4=low threshold value of Threshold 3 (Freq Sep)
In5=low threshold value of Threshold 7 (GAMMA COH)
In6=count output of Counter 2 (Period Timer)
In7=output value of Expression 29 (High Value Compressor)
In8=pass/fail value of Threshold 10 (Thrust Control)
In9=pass/fail value of Threshold 9 (Rotation Index)

These data are processed according to the following logical statement:

If((In6>3 0)&(In8=1)&(In7>1.2)&(In9=1), (MAX (CEIL((In1−In2+In3+In4+(In5*2))*4200), 0)), 0)

IF the period timer is past 30 seconds AND IF the PCT value is above threshold AND IF the altitude is above minimum safe height AND IF the rotation index indicates there is no spin THEN send the integer value of the sum of the low threshold values of Thresholds 1, 2 (Threshold 2 is subtracted because it varies inversely relative to the other values), 3, 6 & 7 (Threshold 7 is doubled to enhance weighting of the PCT value) multiplied by 4200 (initial PPM conversion factor) to Expression 25 (Speed Governor) ELSE IF this value is negative THEN send a null value.

Expression 25 (Speed Governor) receives the output from Expression 16 (FORWARD Base Value) and sets an upper limit on the PPM value for forward thrust:

MIN (In1, 7500)

The lower of the two values will be sent to Expression 31 (THRUST STATUS), Expression 33 (TEST FORWARD THRUST) and Meter 14 (THRUST) with forward thrust responding inversely to the value of Expression 16 (FORWARD Base Value).

Expression 26 (Speed to PPM) receives the output from Expression 33 (TEST FORWARD THRUST) and converts it to the usable range for the PPM software by adding a value of 12,500 then sends this value to Server 1 (In3).

Expression 27 (Basic Control State) (If((In1>30), In2, 1)) receives the output from Counter 2 (Period Timer) (In1) and Expression 28 (Flight Control State) (In2) and provides the flight status control data. IF the period is past the 30-second adjustment delay THEN the value of In2 is sent to Expression 30 (PILOT CONTROL STATUS) ELSE a value of "1" is sent.

Expression 28 (Flight Control State) (If((In1>1.2), 10, 5)) receives the output from Expression 29 (High Value Compressor) and sends it to Expression 27 (Basic Control State). IF the altitude is above the minimum safe value THEN send a value of "10" ELSE send a value of "5".

Expression 30 (PILOT CONTROL STATUS) receives the output from Expression 27 (Basic Control State) (In1), Expression 31 (Thrust Status) (In2) and Expression 24 (ROTATION CALC) (In3) and converts those data into instructions for Video Player 5 (PilotControlStatus) using the following logical statement:

If((In1=10), (In2+(In3/500)), In1)

IF the Basic Control State (In1) indicates flight altitude is above safe minimum THEN send control instruction data to PilotControlStatus ELSE send the value of In1.

| Pilot Control Status Calculations (Output = Video Frame #) | | | | | | |
|---|---|---|---|---|---|---|
| OUTPUT: | 1 | 5 | 30 | 36 | 40 | 56 |
| SOURCE: | Exp27 | Exp28 | Exp24 | Exp24 | Exp24 | Exp24 + 31 |
| CALC: | In1 | In1 | In3/500 | In3/500 | In3/500 | In2 + (In3/500) |
| VERTICAL: | OFF | ON | ON | ON | ON | ON |
| SPIN: | OFF | OFF | RIGHT | NO SPIN | LEFT | NO SPIN |
| THRUST: | OFF | OFF | OFF | OFF | OFF | ON |

Expression 31 (THRUST STATUS) receives input from Expression 25 (Speed Governor) and Threshold 9 (Rotation Index) and sends thrust permission status to Expression 30 (PILOT CONTROL STATUS).

If((In1<1000)|(In2=0), 0, 20)

IF Thrust is too low OR UFO is spinning THEN 0=No Thrust Allowed ELSE 20=Thrust On.

Expression 32 (NO SPIN Tone) receives input from Expression 24 (Rotation Calc). When there is no rotational signal, send a positive value ("1") to Audio Player 2 (No Spin).

Expression 33 (TEST FORWARD THRUST) receives input from Expression 25 (Speed Governor) and Counter 2 (Period Timer) and signals a maximal lateral rotor burst to initialize the Forward Thrust chip.

If(((In2>13)&(In2<18)), 9500, In1)

IF the period timer is between 13 AND 18 seconds THEN send a maximal burst signal to Expression 26 (Speed to PPM) ELSE pass through forward thrust data.

Expression 34 (LATERAL ROTOR TEST ALERT) receives input from Expression 30 (Pilot Control Status) and Counter 2 (Period Timer) and controls the video alert for a maximal lateral rotor burst to initialize the Forward Thrust chip controlled by Expression 33 (TEST FORWARD THRUST).

If((In2>12)&(In2<20), 70, In1)

IF the period timer is between 12 AND 20 seconds THEN send video alert data to Video Player 5 (PilotControlStatus) (Frame #70) ELSE pass through data from Expression 30.

Expression 35 (Flight Start Record) receives input from Counter 2 (Period Timer) and signals Trend 4 (FLIGHT RECORD) to place a vertical red bar at the start of each flight record.

Expression 41 (EEG Status Control) receives data from Expression 35 and directs the video file, BL.avi, to display either frame #1 or frame #8.

If((In1=4), 1, 8)

The Threshold Calculator Includes:

Threshold 10 (Thrust Control) receives the output from Expression 8 (PCT Calculation) with a base tolerance of 60% success and 250 ms averaging. Auto-threshold control is from the pass/fail output of Threshold 9 (Rotation Index: A/T Ratio). When the pass condition is met, a value of "1" is sent to In8 of Expression 16 (FORWARD Base Value).

The Score Devices Include:

Score 1 (F CTRL/FLT) receives output from Sample/Hold 2 and displays a running total for each period of full control events as calculated by Counter 7 (FRWD Count). Reset instructions are received from NOT 4. Sound output is not enabled.

Score 2 (FULL CONTROL TTL) receives data from the trigger output of Counter 7 (FRWD Count) and displays the running total of full control events throughout the entire session. Sound output is enabled so that a bell tone is heard with each event. The sound file is "ding.wav".

The Audio Player Includes:

Audio Player 2 (No Spin) receives input from Expression 32 (NO SPIN Tone) into the Trigger input which activates the audio file, "UFO Steady.wav". Volume is set to 30, and both the "repeat" and "restart on trigger" functions are selected.

The Video Players Include:

Video Player 5 (PilotControlStatus) receives the output from Expression 34 and presents the status messages for Vertical, Spin, and Thrust controls as calculated in Expression 30 as well as the alert message for the Rotor Test during the calibration period. The video file is "ControlStatus3d.avi". Input directs the video object to the specific frame in the video file containing the appropriate message with no averaging.

Video Player 8 (Forward Thrust) receives the output from Expression 25 (Speed Governor) and presents a video representation that provides proportional feedback relative to the values calculated in Expression 16. The video file is "Thrust.avi". Input directs the video object to respond within the range of 0-6K with 0.5 sec averaging.

Video Player 9 (EEG Status) receives the output from Expression 41 (EEG Status Control) and presents the status message for the EEG link. The video file is "BL.avi". Input directs the video object to the specific frame in the video file containing the appropriate message with no averaging.

The Server Object is Described as Follows:

Server 1 (LINK to RF TRANS) receives three outputs as follows:

In1=AMPLITUDE BALANCE OUTPUT (Rotation): Source=Expression 24 (ROTATION CALC)
In2=RATIO OUTPUT (Vertical): Source=Expression 22 (Start Delay)
In3=DIRECT PCT OUTPUT (Forward thrust): Source=Expression 26 (Speed to PPM)

These data streams are made available to a PPM conversion program: SC8000MFC4.exe which has been modified specifically to receive data from the BioExplorer Server object. These data are transmitted through I/O COM4 which is activated by running: HidCommInst.exe. These are the controlling data for the external objects, devices or displays.

Module X Contains the Neural Net and Auto-Logic Cascades.

Module 10 (or "X") permits this software design to adapt to individual users. The two neural nets are: 1) Primary Threshold Control for processing data input and 2) Pilot Threshold Control Assist for processing data output.

The Primary Threshold Control Cascade Includes:

Step 1 at OR 2 (NN ON) which controls Step 2 as follows: IF coherence frequency dispersion is low (NOT 1) OR IF Low Power Assist is engaged (Expression 43) THEN allow Alpha-theta Coherence (Threshold 1) to adjust threshold value.

Step 2 at Threshold 1 (Incr Alpha Coh) which controls Step 3 as follows: IF Alpha-theta Coherence is doing well (above threshold) THEN allow Frequency Separation (Threshold 3) to adjust threshold value.

Step 3 at Threshold 3 (Freq Sep) which controls Steps 4a & 4b as follows: IF Frequency Separation is doing well (above threshold) THEN allow BOTH Alpha Synchrony (Threshold 4) AND Alpha/Theta Ratio (Threshold 5) to adjust limits.

Step 4 is Alpha-Theta Amplitude Controls which includes:

Step 4a, Threshold 4 (Alpha Sync), which controls Step 5a as follows: IF Alpha Synchrony is doing well (within threshold limits) THEN allow Beta Coherence (Threshold 2) to adjust threshold value; and Step 4b, Threshold 5 (A-T Ratio), which controls Step 5b as follows: IF Alpha/Theta Ratio is doing well (within threshold limits) THEN allow SMR Coherence (Threshold 6) to adjust threshold value.

Step 5 is Beta Coherence Controls which includes:

Step 5a, Threshold 2 (Deer Beta Coh), and Step 5b, Threshold 6 (SMR COH).

Step 6 is at Expression 9 which controls Step 7 as follows: IF combined threshold outputs (PCT data stream, Expression 8) exceed minimum value THEN allow GAMMA COH (Threshold 7) to adjust threshold value.

Step 7, Threshold 7 (GAMMA COH), is the outermost point on the input auto-logic cascade.

The Pilot Threshold Control Assist includes:

Step P1 at Threshold 8 (GATE STATUS) which controls Step P2 as follows: IF PCT Gate is open THEN allow Rotation Index (Threshold 9) to adjust limits.

Step P2 at Threshold 9 (Rotation Index A/T Ratio) which controls Step P3 as follows: IF Rotation Control is hovering near center (no rotation) THEN allow Thrust Control (Threshold 10) to adjust threshold values.

Step P3 at Threshold 10 (Thrust Control) which is the outermost point on the output auto-logic cascade.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of converting brainwave signals into a control signal, the method comprising the steps of:
    receiving a brainwave signal;
    generating a first value and a second value based on the received brainwave signal, wherein the first value is different from the second value;
    calculating a ratio between the first and second values, wherein the calculation comprises (first value−second value)/(first value+second value);
    comparing the ratio to a predetermined threshold, wherein the predetermined threshold is between −1 and +1;
    outputting a first control signal based on the comparison of the ratio to the predetermined threshold;
    determining whether the ratio satisfies the predetermined threshold; and
    increasing the predetermined threshold when it is determined that the ratio satisfies the predetermined threshold and decreasing the predetermined threshold when it is determined that the ratio does not satisfy the predetermined threshold.

2. The method of claim 1 wherein the first value and the second value are generated by determining a coherence between the received brainwave signal and a second received brainwave signal.

3. The method of claim 2 wherein the first value comprise determining the coherence between the received brain wave signal and the second brainwave signal in a first predetermined frequency range and the second value comprises determining the coherence between the received brain wave signal and second brainwave signal in a second predetermined frequency range.

4. The method of claim 3 wherein the first predetermined frequency range is between approximately 2 Hz and 50 Hz.

5. The method of claim 4 wherein the second predetermined frequency range is between approximately 2 Hz and 50 Hz.

6. The method of claim 1 further comprising a third value and a fourth value, wherein the third value is different from the first and second values and the fourth value is different from the first, second, and third values, and further comprising
    calculating a second ratio wherein the second ratio calculation comprises (third value−fourth value)/(third value+fourth value);
    comparing the second ratio to a predetermined second threshold, wherein the predetermined threshold is between −1 and +1; and
    outputting a second control signal based on the comparison of the second ratio to the predetermined second threshold.

7. The method of claim 6 wherein the third and fourth values are calculated by comparing a power of at least one brainwave signal.

8. The method of claim 6 wherein the third value is the amplitude of a portion of the brainwave signal and the fourth value is the amplitude of another signal.

9. The method of claim 8 wherein the another signal is another brainwave signal.

* * * * *

UNITED STATES PATENT AND TRADEMARK OFFICE
CERTIFICATE OF CORRECTION

| | | |
|---|---|---|
| PATENT NO. | : 9,020,587 B2 | Page 1 of 1 |
| APPLICATION NO. | : 13/676519 | |
| DATED | : April 28, 2015 | |
| INVENTOR(S) | : Green et al. | |

It is certified that error appears in the above-identified patent and that said Letters Patent is hereby corrected as shown below:

In the Specification

Column 18, line 49, delete "Deer" and insert --Decr--

Column 21, line 44, delete "euphonies" and insert --euphonics--

Column 26, line 10, delete "AB" and insert --A/B--

Column 32, line 29, delete "Deer" and insert --Decr--

Signed and Sealed this
Tenth Day of November, 2015

Michelle K. Lee
*Director of the United States Patent and Trademark Office*